(12) United States Patent
Kandori et al.

(10) Patent No.: US 10,959,701 B2
(45) Date of Patent: Mar. 30, 2021

(54) PROBE, TRANSDUCER UNIT, AND SUBJECT INFORMATION ACQUISITION APPARATUS

(71) Applicant: CANON KABUSHIKI KAISHA, Tokyo (JP)

(72) Inventors: Atsushi Kandori, Ebina (JP); Masahiro Okuda, Sagamihara (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 557 days.

(21) Appl. No.: 15/528,074

(22) PCT Filed: Nov. 18, 2015

(86) PCT No.: PCT/JP2015/005756
§ 371 (c)(1),
(2) Date: May 18, 2017

(87) PCT Pub. No.: WO2016/084344
PCT Pub. Date: Jun. 2, 2016

(65) Prior Publication Data
US 2017/0319179 A1  Nov. 9, 2017

(30) Foreign Application Priority Data

Nov. 28, 2014 (JP) .............................. JP2014-242445
Nov. 6, 2015 (JP) ................................. 2015-218781

(51) Int. Cl.
*A61B 8/00* (2006.01)
*B06B 1/06* (2006.01)
(Continued)

(52) U.S. Cl.
CPC .......... *A61B 8/4494* (2013.01); *A61B 5/0095* (2013.01); *A61B 5/708* (2013.01);
(Continued)

(58) Field of Classification Search
CPC ................ A61B 8/4494; A61B 5/0095; A61B 2562/046; A61B 5/708; A61B 8/4477;
(Continued)

(56) References Cited

U.S. PATENT DOCUMENTS

2004/0102700 A1\* 5/2004 Asafusa .................. A61B 8/13
600/437
2005/0169107 A1  8/2005 Thomenius
(Continued)

FOREIGN PATENT DOCUMENTS

EP  1491914 A2  12/2004
EP  2775274 A2  9/2014
(Continued)

*Primary Examiner* — Bill Thomson
*Assistant Examiner* — Aminah Asghar
(74) *Attorney, Agent, or Firm* — Canon U.S.A., Inc. IP Division

(57) ABSTRACT

To provide a photoacoustic probe capable of acquiring subject information for reducing generation of artifacts without increasing the number of wires connected to the outside. Provided is a probe including a plurality of ultrasonic transducers, wherein the ultrasonic transducers are divided into a plurality of groups, two adjoining ultrasonic transducers belong to different groups, and the probe includes a group selection unit configured to switch signals of the ultrasonic transducers to be outputtable for each of the groups.

14 Claims, 33 Drawing Sheets

(51) Int. Cl.
    *B06B 1/02*     (2006.01)
    *G01N 29/24*     (2006.01)
    *G01H 11/06*     (2006.01)
    *G10K 11/34*     (2006.01)
    *G01N 29/22*     (2006.01)
    *A61B 8/08*     (2006.01)
    *G10K 11/32*     (2006.01)
    *A61B 5/00*     (2006.01)

(52) U.S. Cl.
    CPC .......... *A61B 8/4477* (2013.01); *A61B 8/5269* (2013.01); *B06B 1/0292* (2013.01); *B06B 1/0637* (2013.01); *G01H 11/06* (2013.01); *G01N 29/22* (2013.01); *G01N 29/221* (2013.01); *G01N 29/223* (2013.01); *G01N 29/2406* (2013.01); *G01N 29/2412* (2013.01); *G01N 29/2418* (2013.01); *G10K 11/32* (2013.01); *G10K 11/345* (2013.01); *A61B 2562/0204* (2013.01); *A61B 2562/046* (2013.01); *G01N 2291/106* (2013.01)

(58) Field of Classification Search
    CPC . A61B 8/5269; A61B 2562/0204; A61B 6/54; A61B 6/563; G01N 2291/106; G01N 29/223; G01N 29/22; G01N 29/2406; G01N 29/221; G01N 29/2412; G01N 29/2418; G10K 11/345; G10K 11/32; B06B 1/0637; B06B 1/0292; G01H 11/06
    See application file for complete search history.

(56) References Cited

U.S. PATENT DOCUMENTS

| | | | |
|---|---|---|---|
| 2005/0228277 A1* | 10/2005 | Barnes | G01S 15/8925 600/437 |
| 2011/0198968 A1* | 8/2011 | Sato | B06B 1/0629 310/317 |
| 2011/0227448 A1* | 9/2011 | Kandori | A61B 5/0095 310/300 |
| 2011/0306865 A1 | 12/2011 | Thornton | |
| 2014/0155751 A1* | 6/2014 | Banjanin | G01S 7/5208 600/447 |
| 2014/0243673 A1* | 8/2014 | Anand | G01S 15/8927 600/447 |
| 2015/0313575 A1* | 11/2015 | Tanaka | A61B 8/145 600/447 |
| 2016/0016198 A1* | 1/2016 | Emadi | B06B 1/0292 367/7 |

FOREIGN PATENT DOCUMENTS

| | | |
|---|---|---|
| JP | H08-024257 A | 1/1996 |
| JP | H11-318889 A | 11/1999 |
| JP | 2005-218684 A | 8/2005 |
| JP | 2011-172621 A | 9/2011 |
| JP | 2012-5624 A | 1/2012 |
| JP | 2012-179348 A | 9/2012 |
| JP | 2014-94111 A | 5/2014 |
| WO | 2014/088079 A1 | 6/2014 |

\* cited by examiner

[Fig. 1A]
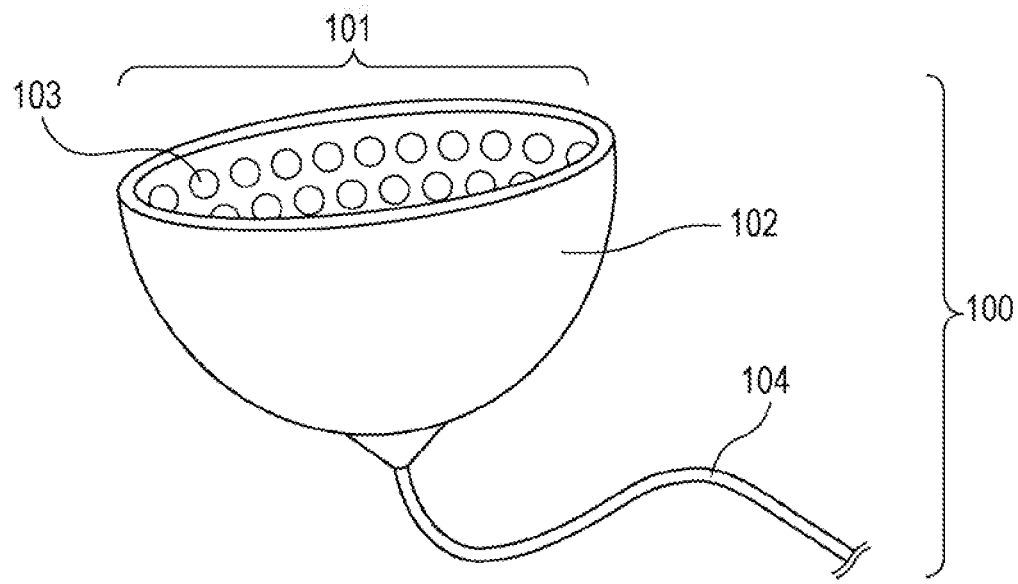
[Fig. 1B]
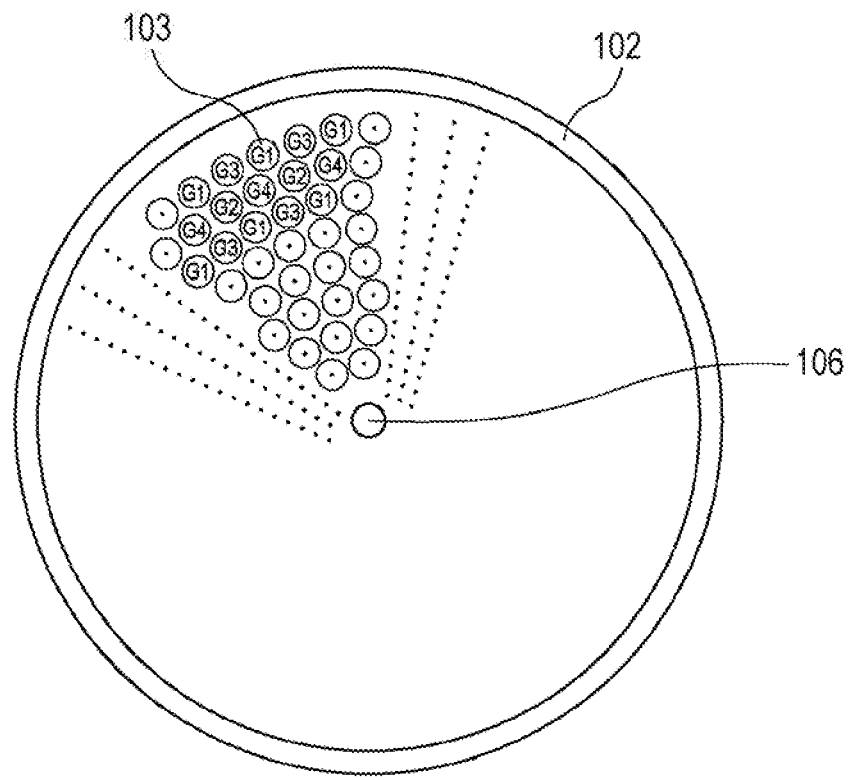

[Fig. 1C]
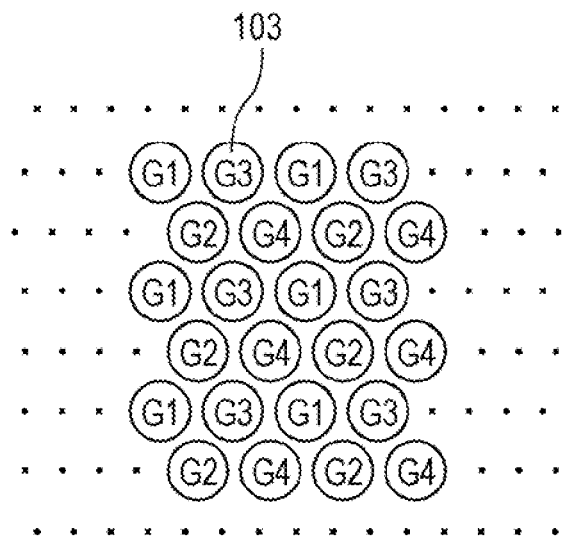
[Fig. 1D]
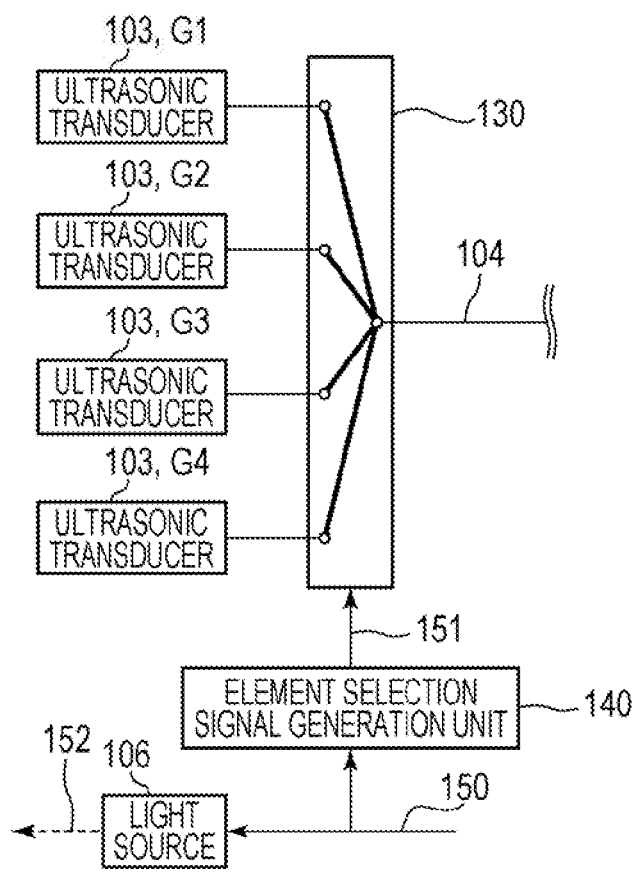

[Fig. 2A]
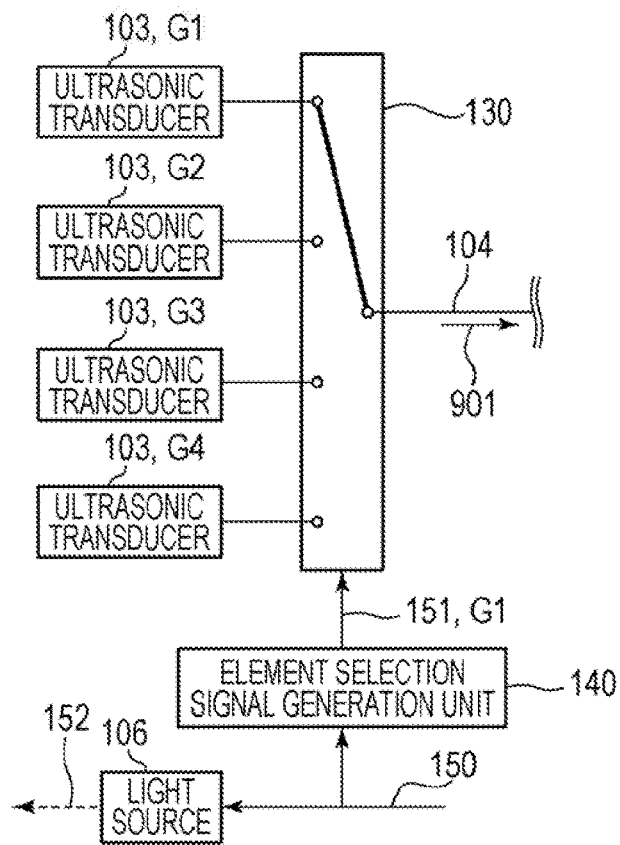
[Fig. 2B]
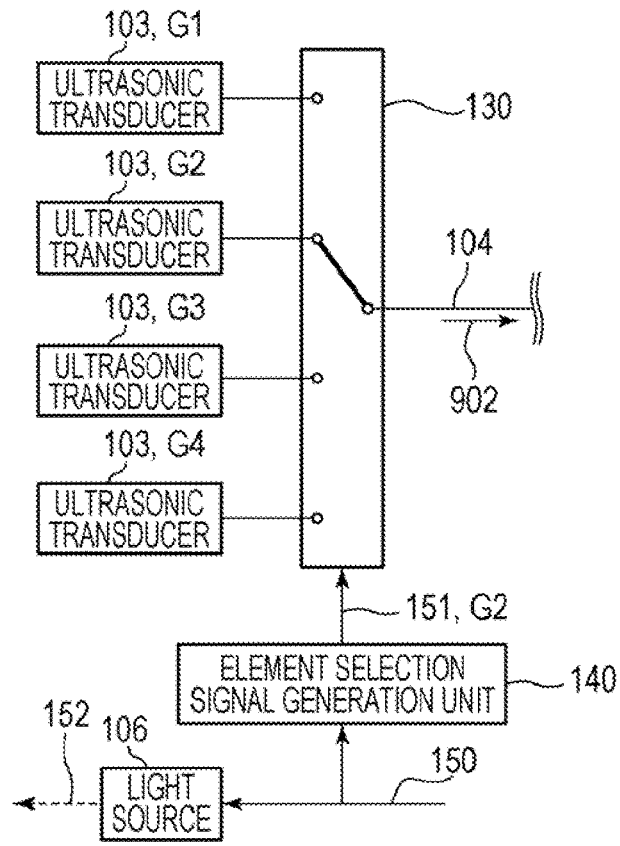

[Fig. 2C]
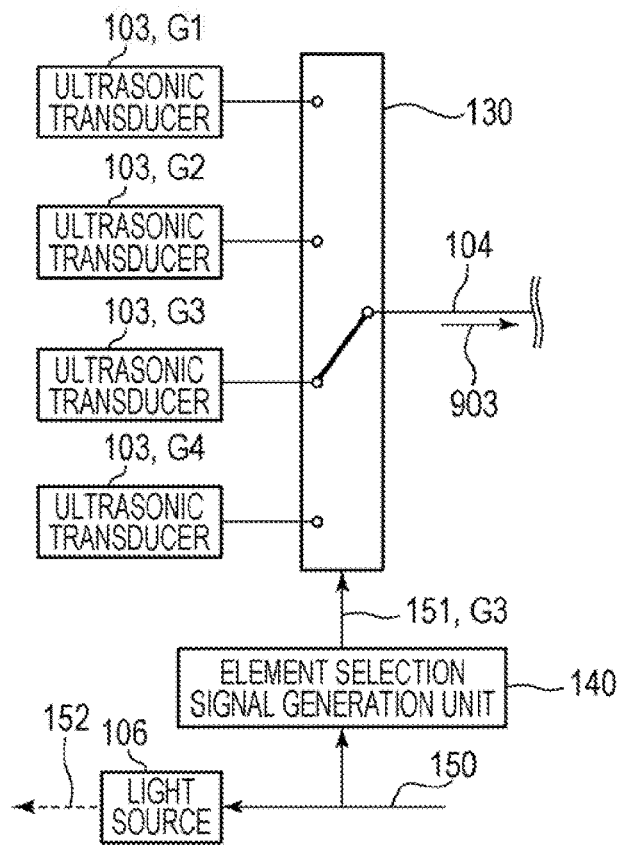
[Fig. 2D]
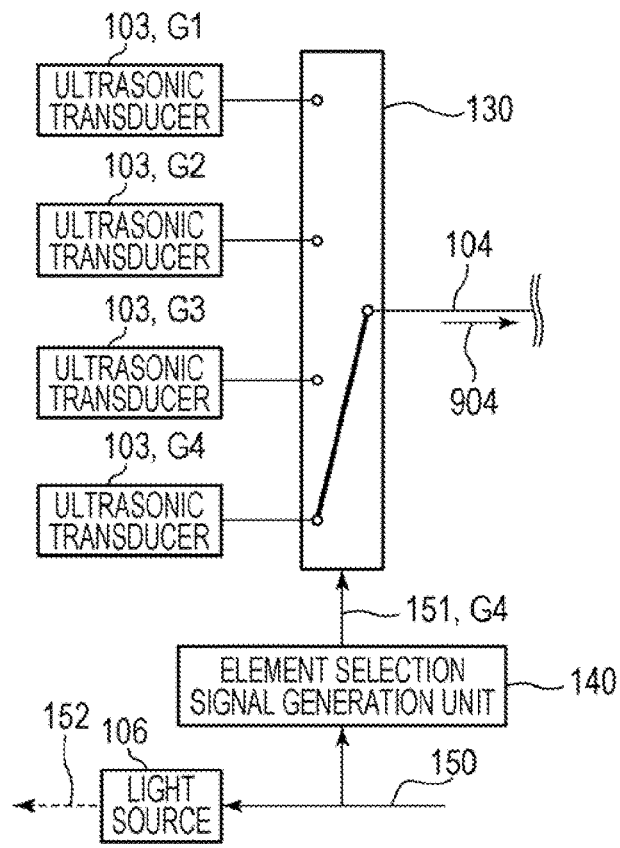

[Fig. 3A]
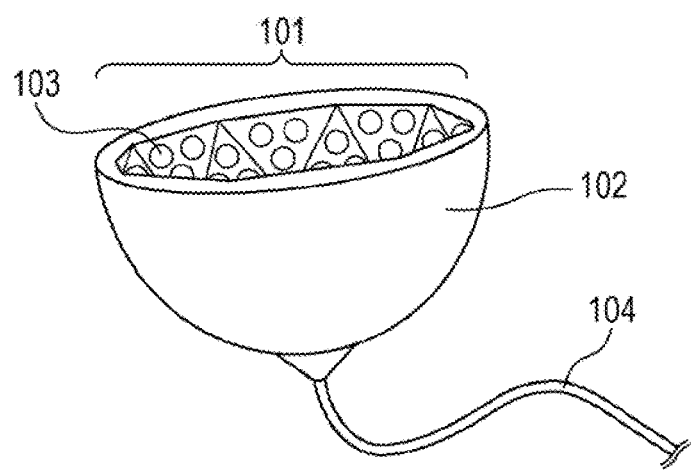
[Fig. 3B]
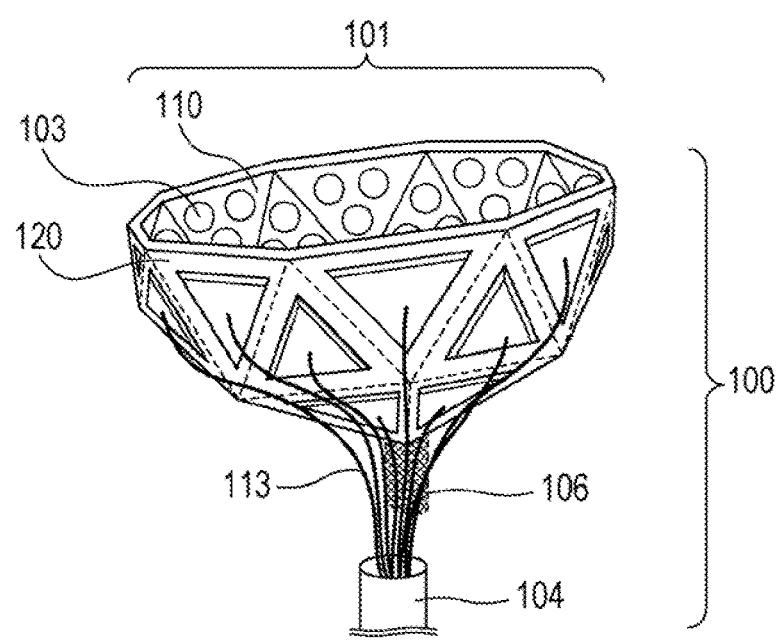
[Fig. 3C]
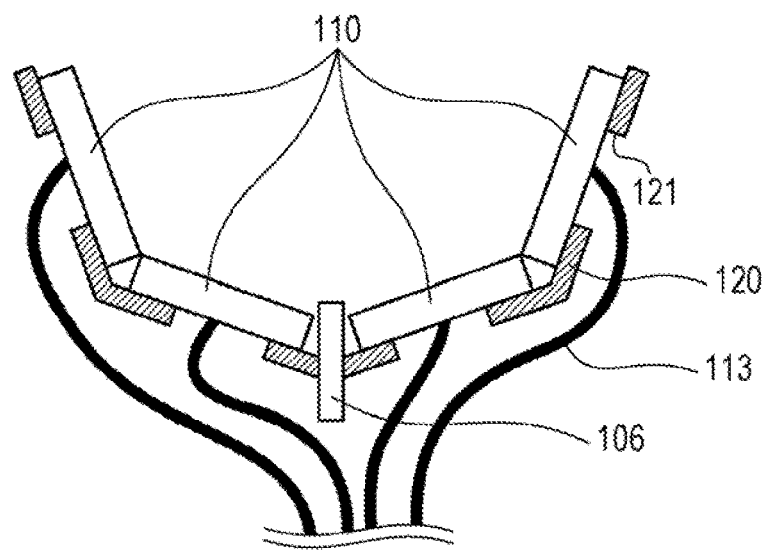

[Fig. 4A]
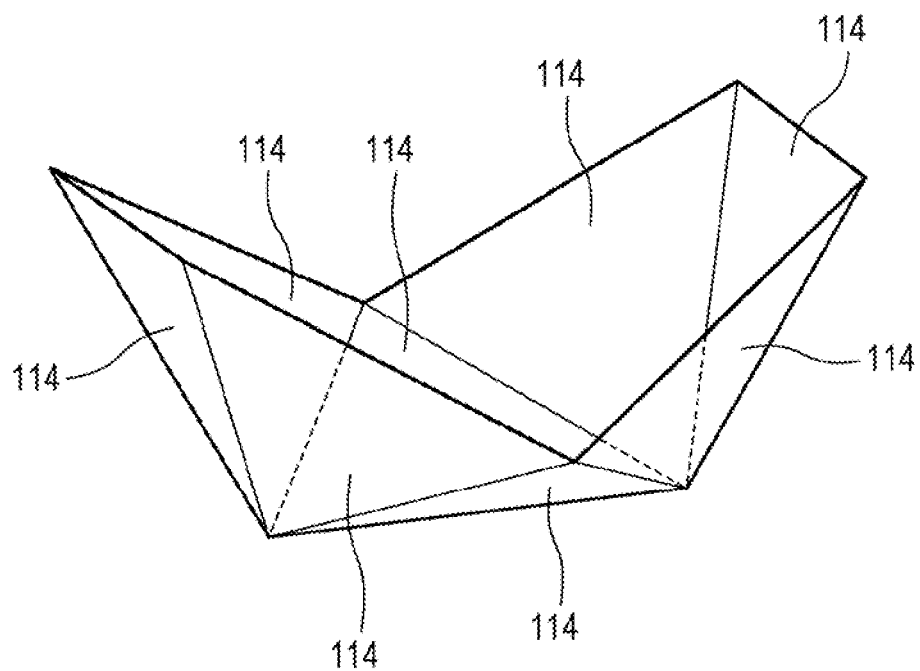
[Fig. 4B]
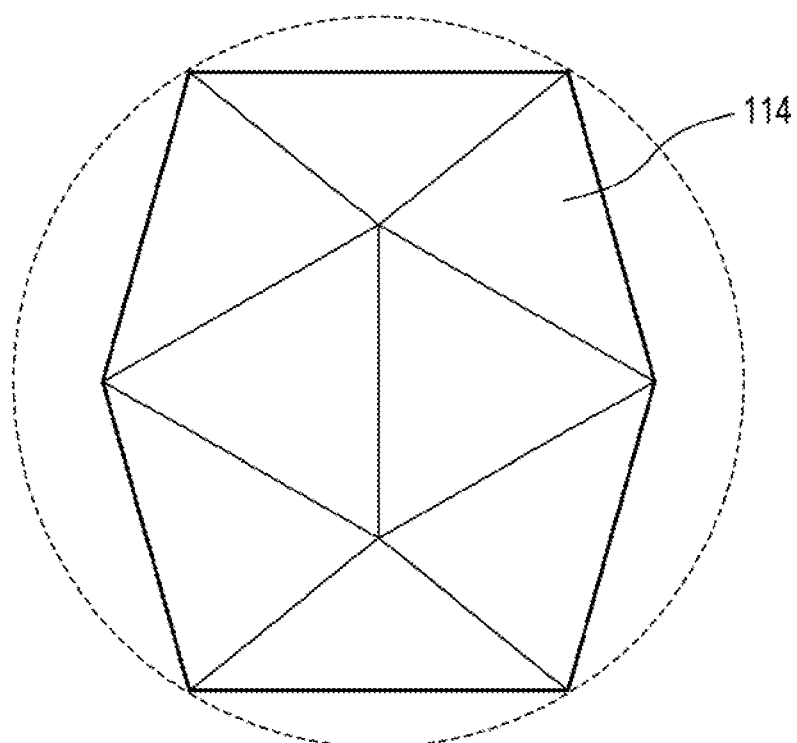

[Fig. 4C]
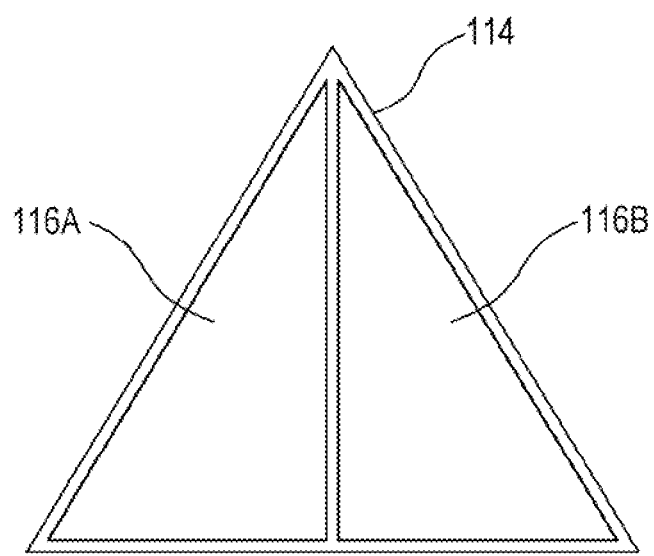
[Fig. 4D]
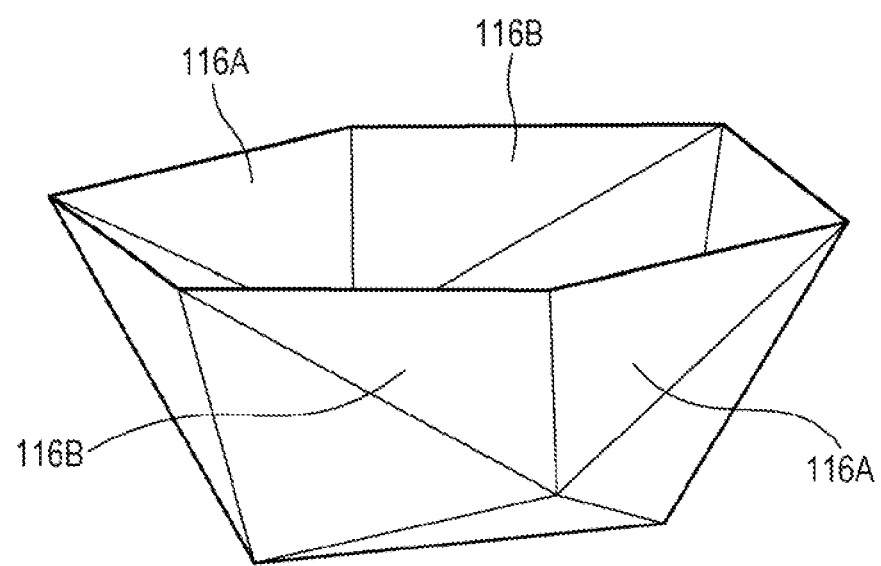

[Fig. 5A]
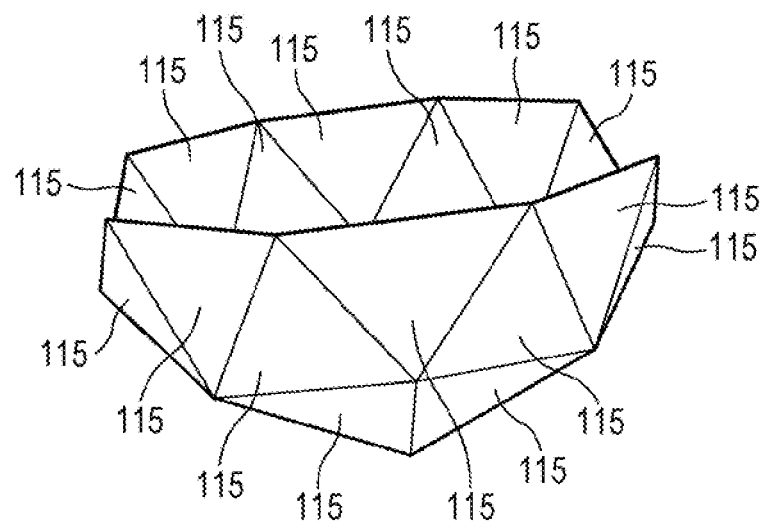
[Fig. 5B]
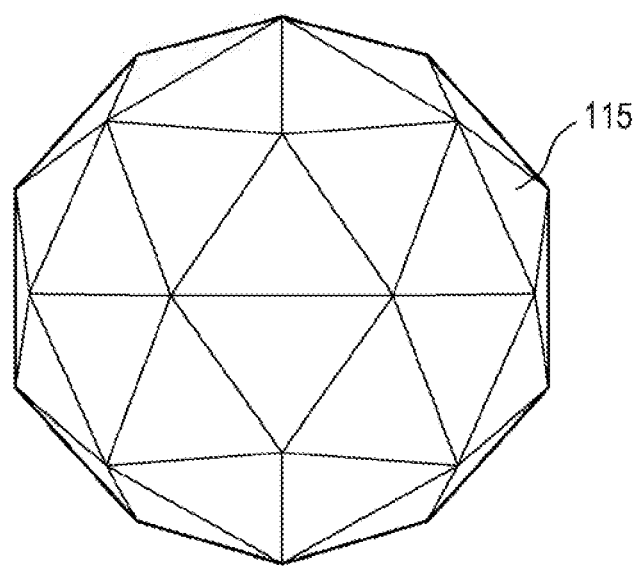
[Fig. 5C]
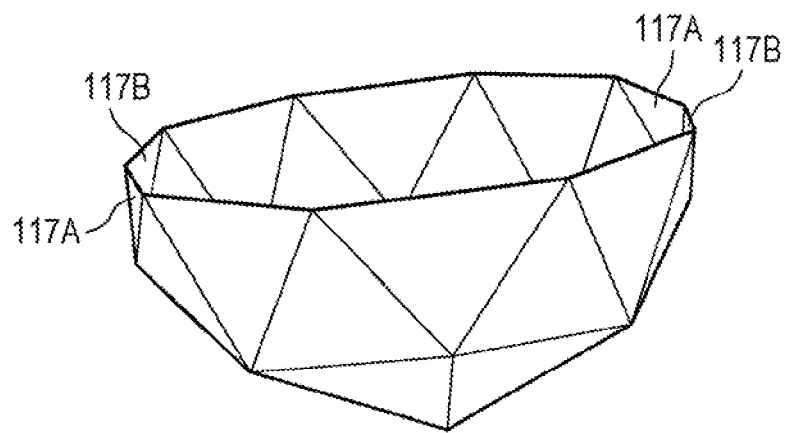

[Fig. 6A]
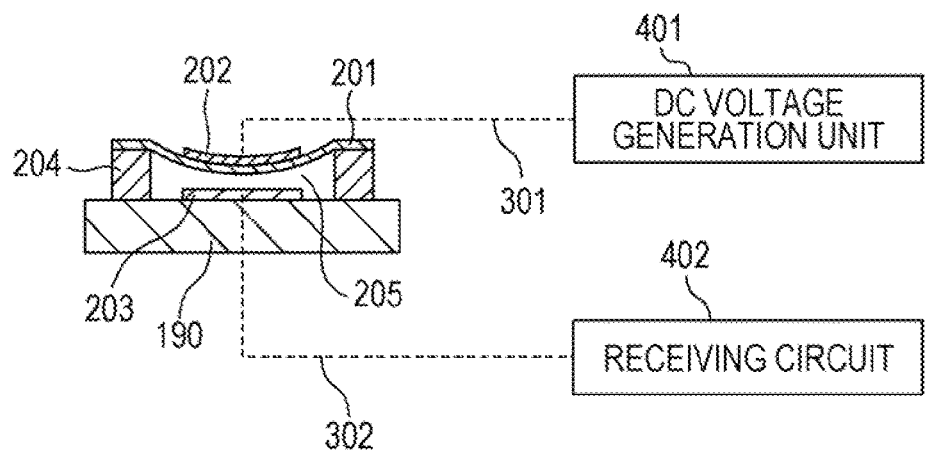
[Fig. 6B]
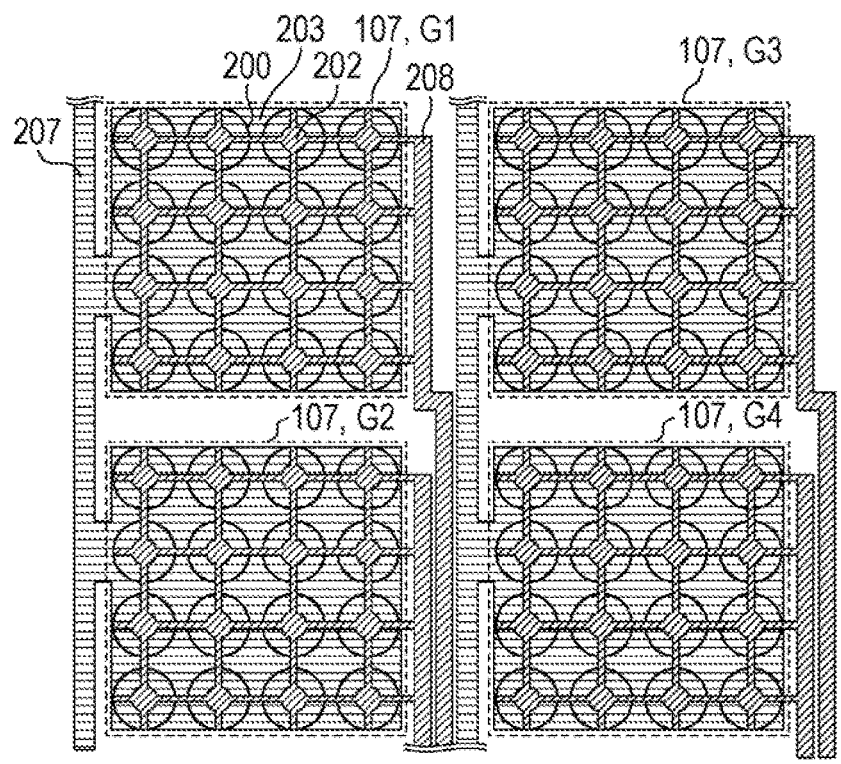
[Fig. 6C]
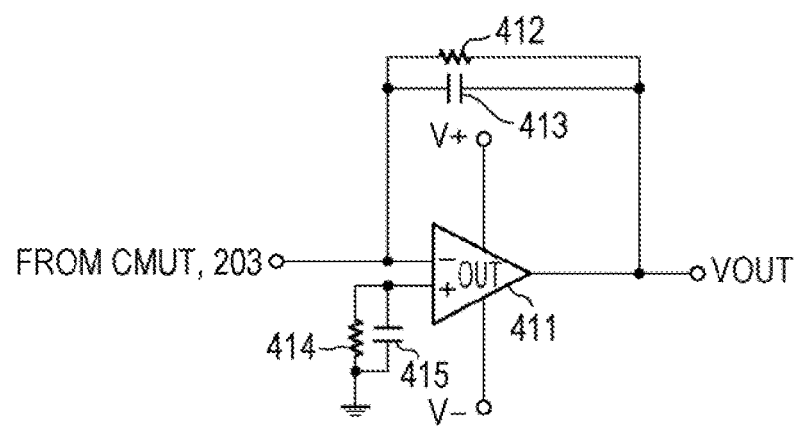

[Fig. 7A]
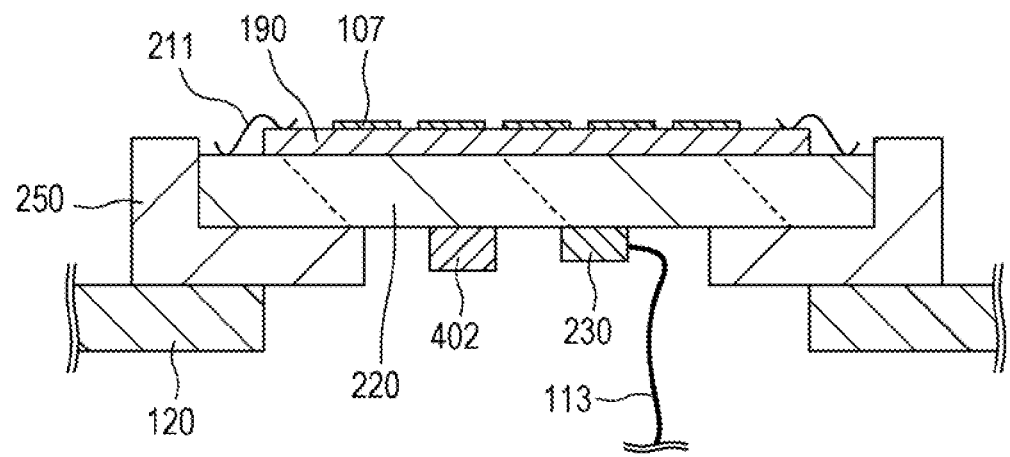
[Fig. 7B]
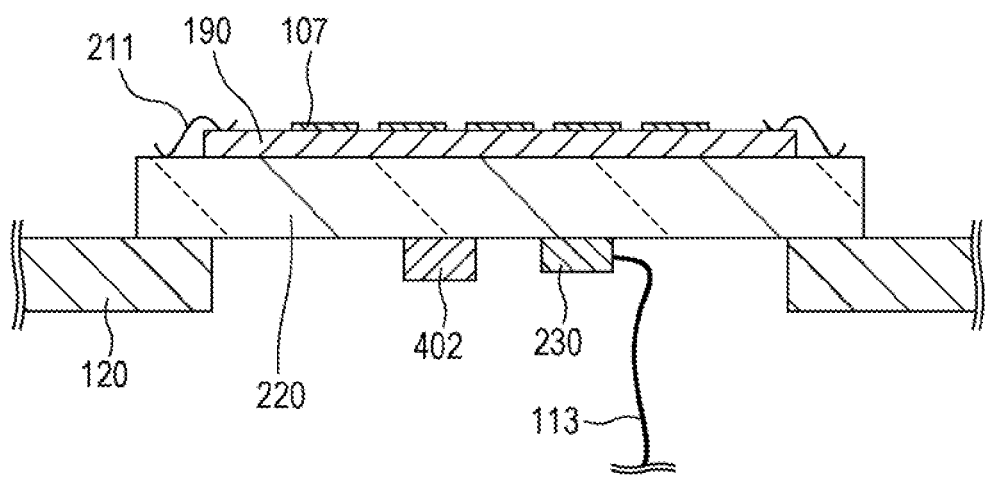

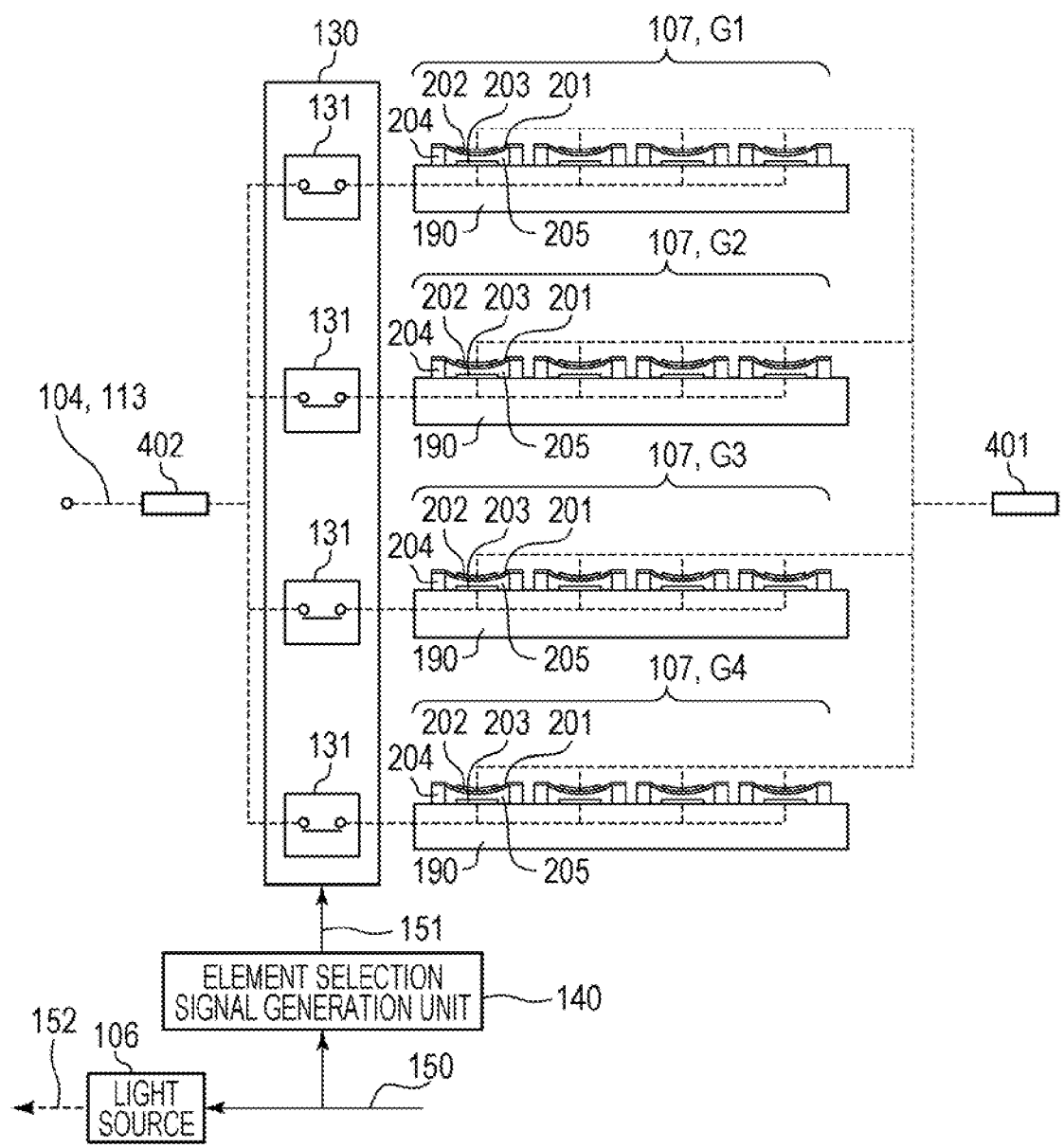
[Fig. 8A]

[Fig. 8B]
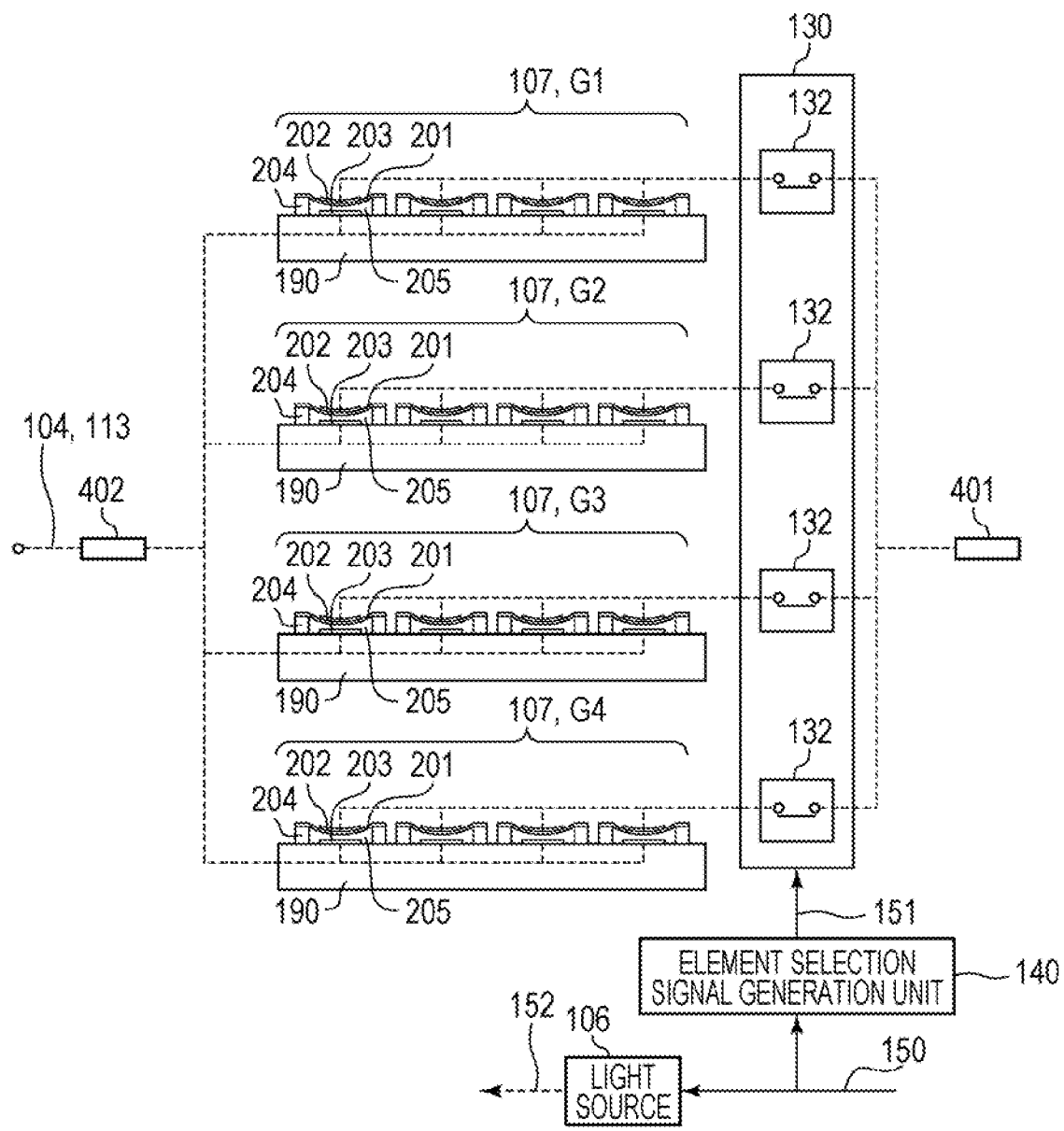

[Fig. 9A]
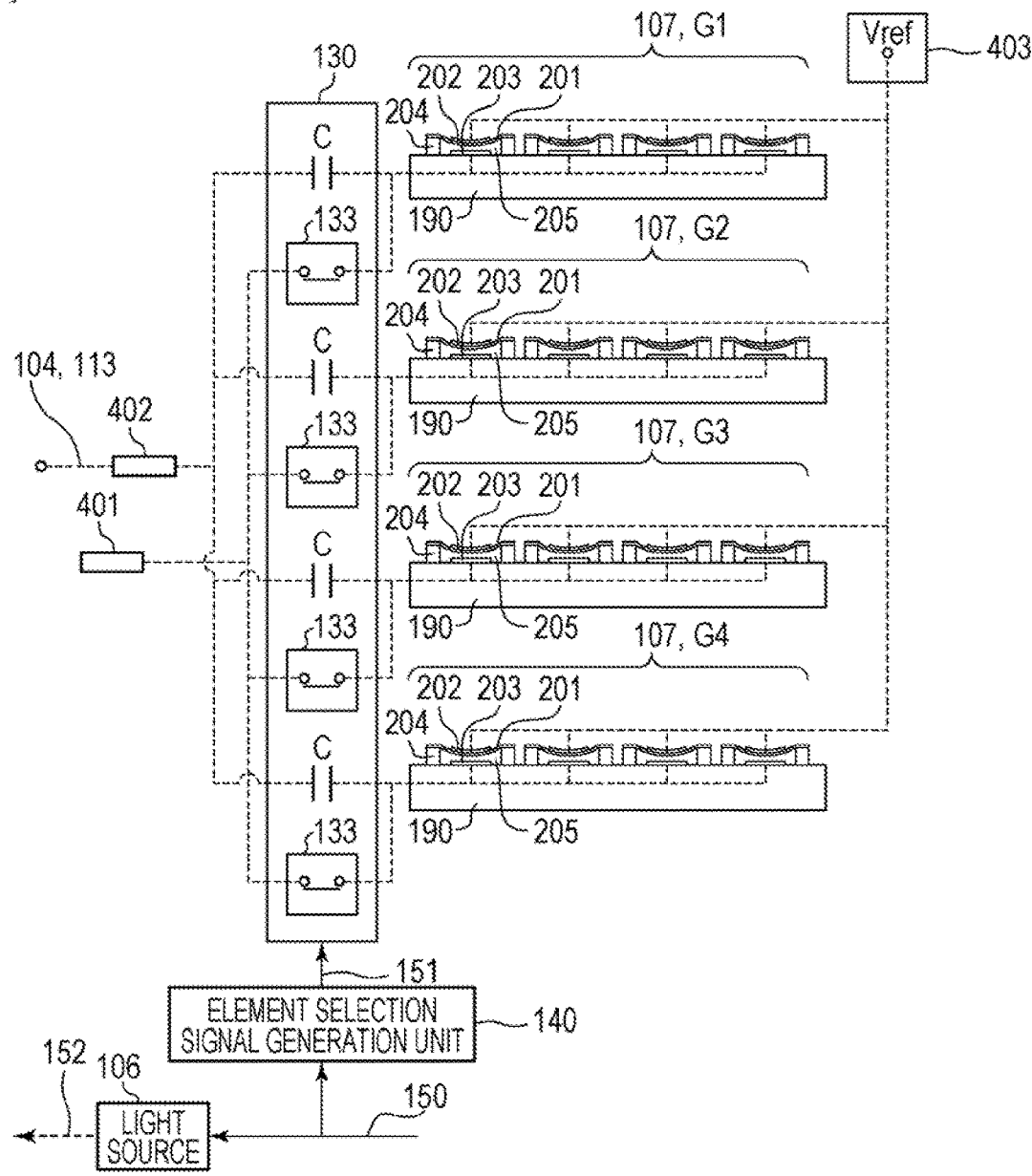
[Fig. 9B]
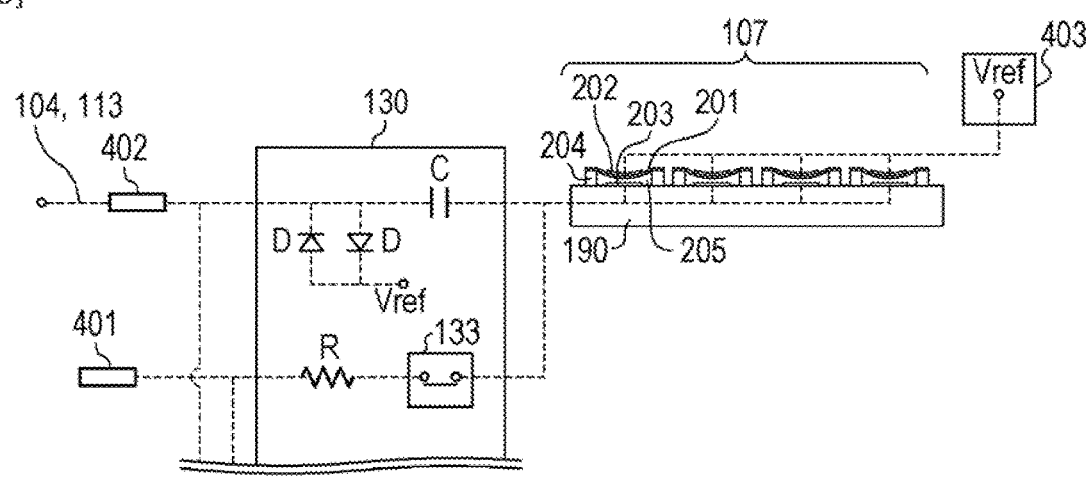

[Fig. 10A]
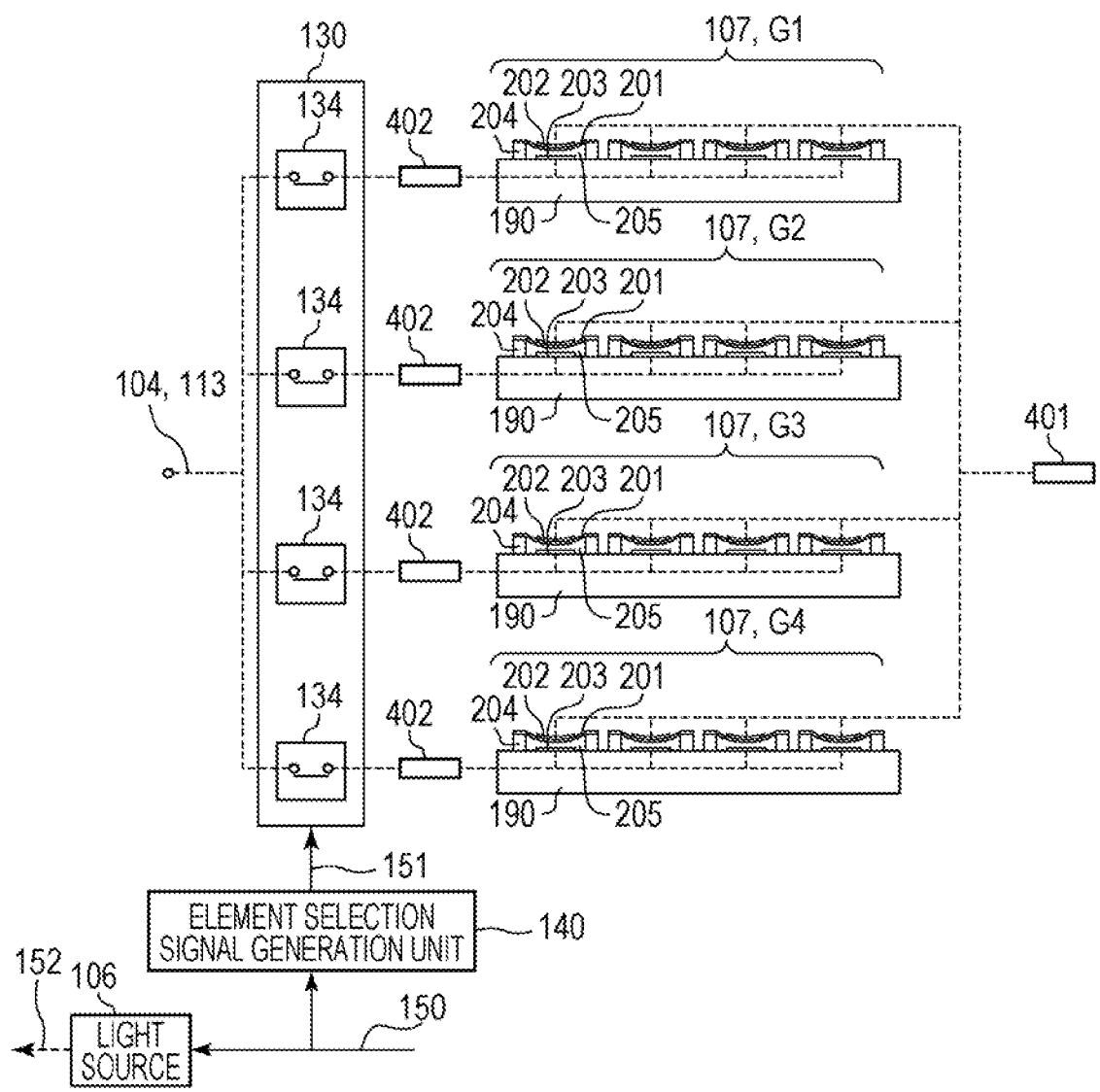

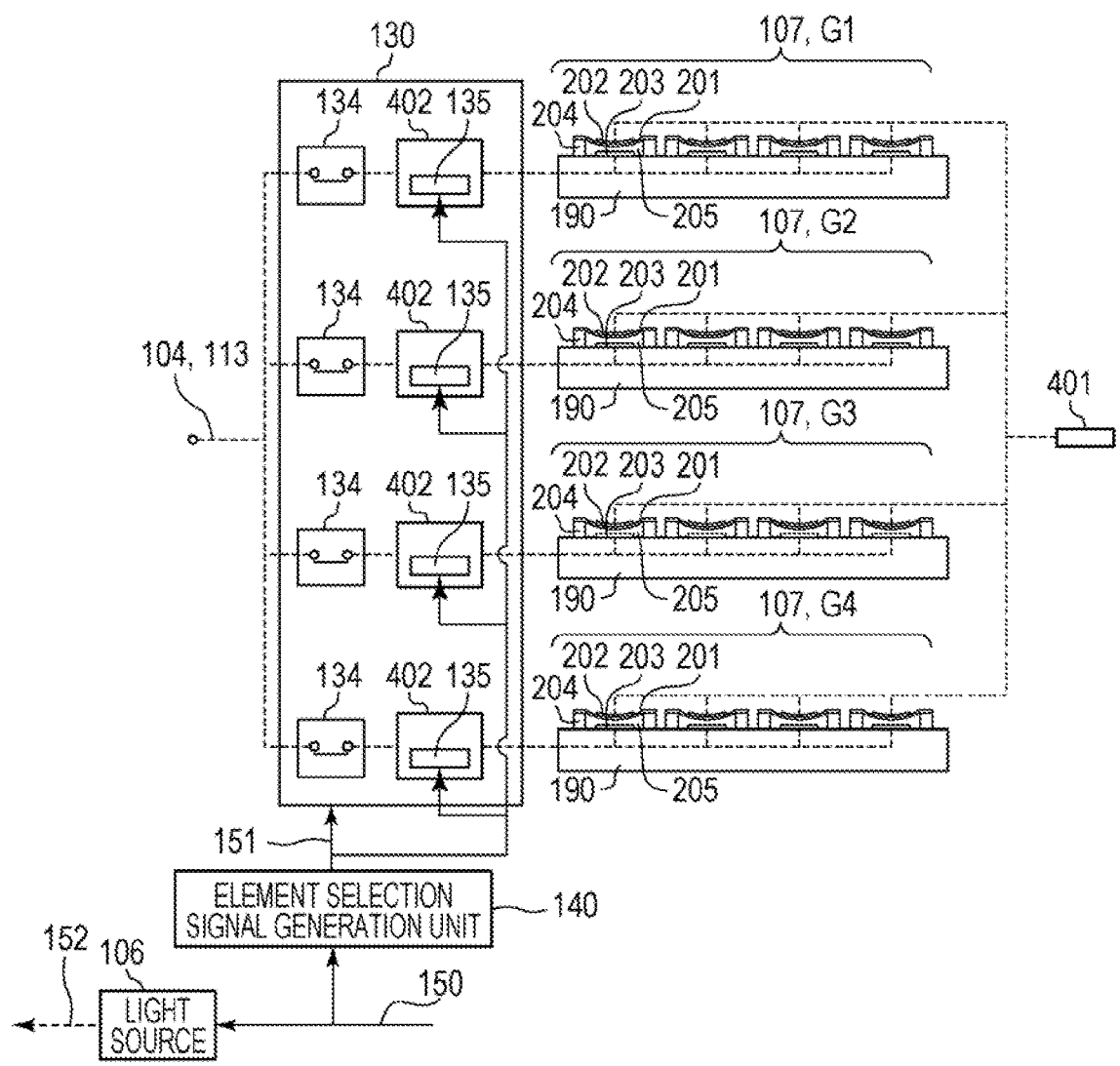
[Fig. 10B]

[Fig. 10C]
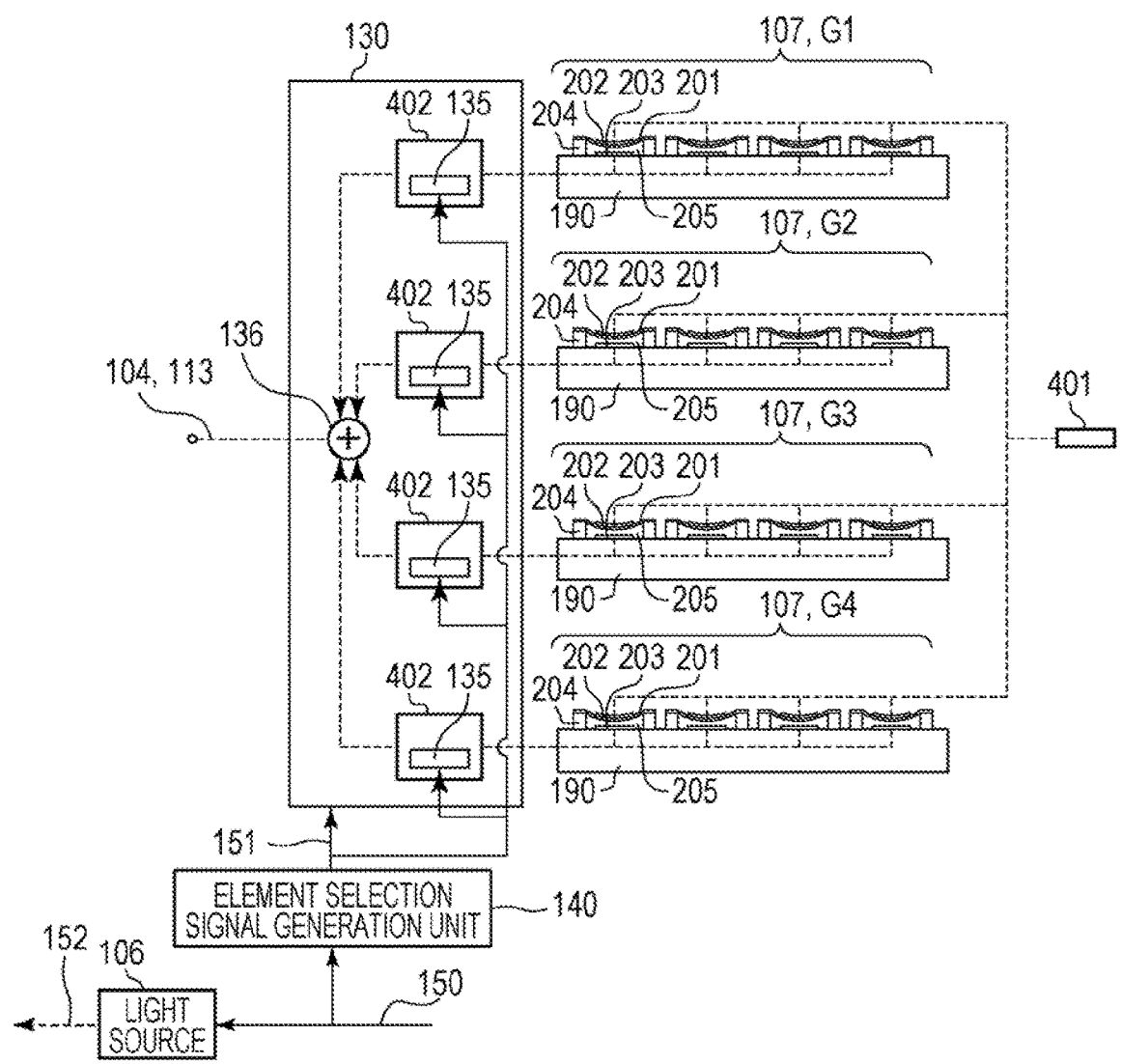

[Fig. 11A]

|  | | | G4 (S1) | (S3) | G2 (S1) | (S3) | G4 (S1) | (S3) |
|  | | | (S2) | (S4) | (S2) | (S4) | (S2) | (S4) |
|  | | | G3 (S1) | (S3) | G1 (S1) | (S3) | G3 (S1) | (S3) |
|  | | | (S2) | (S4) | (S2) | (S4) | (S2) | (S4) |
|  | | | G4 (S1) | (S3) | G2 (S1) | (S3) | G4 (S1) | (S3) |
|  | | | (S2) | (S4) | (S2) | (S4) | (S2) | (S4) | a

| G4 | G2 | G4 |
| G3 | G1 | G3 |
| G4 | G2 | G4 |

[Fig. 11C]
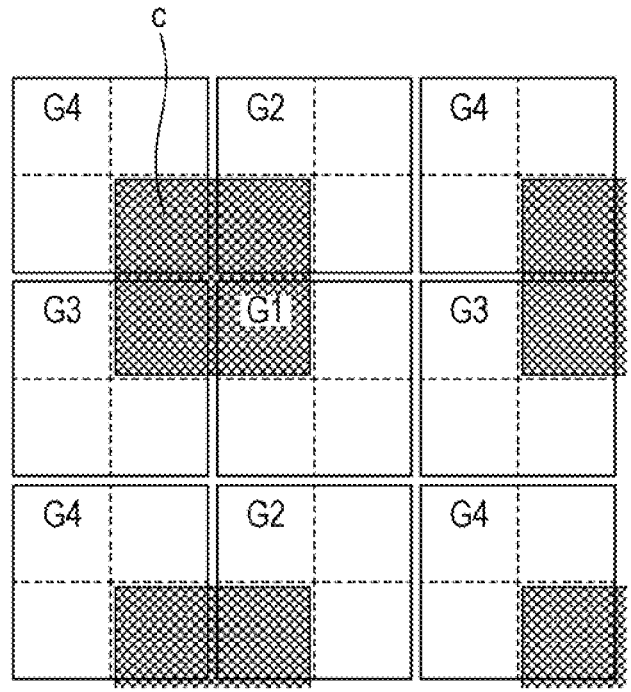
[Fig. 11D]
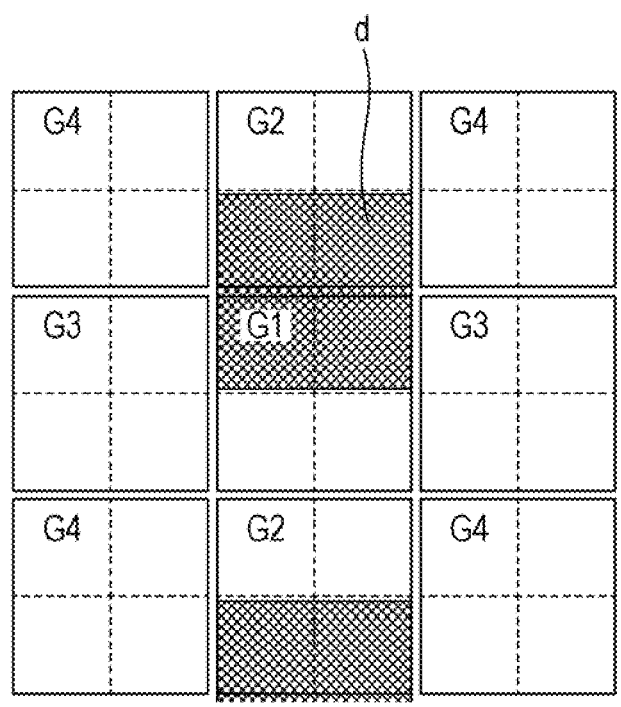

[Fig. 12A]
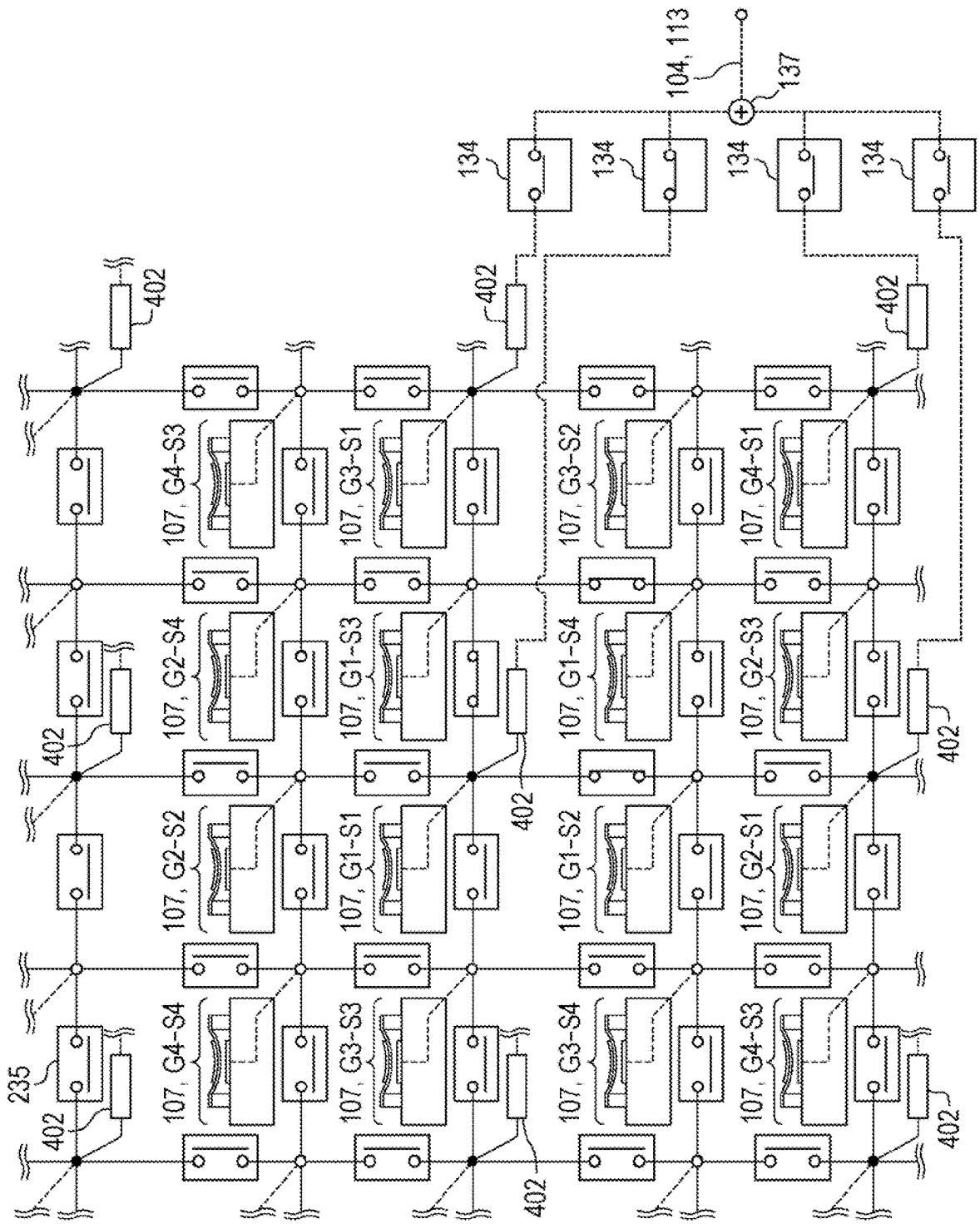

[Fig. 12B]
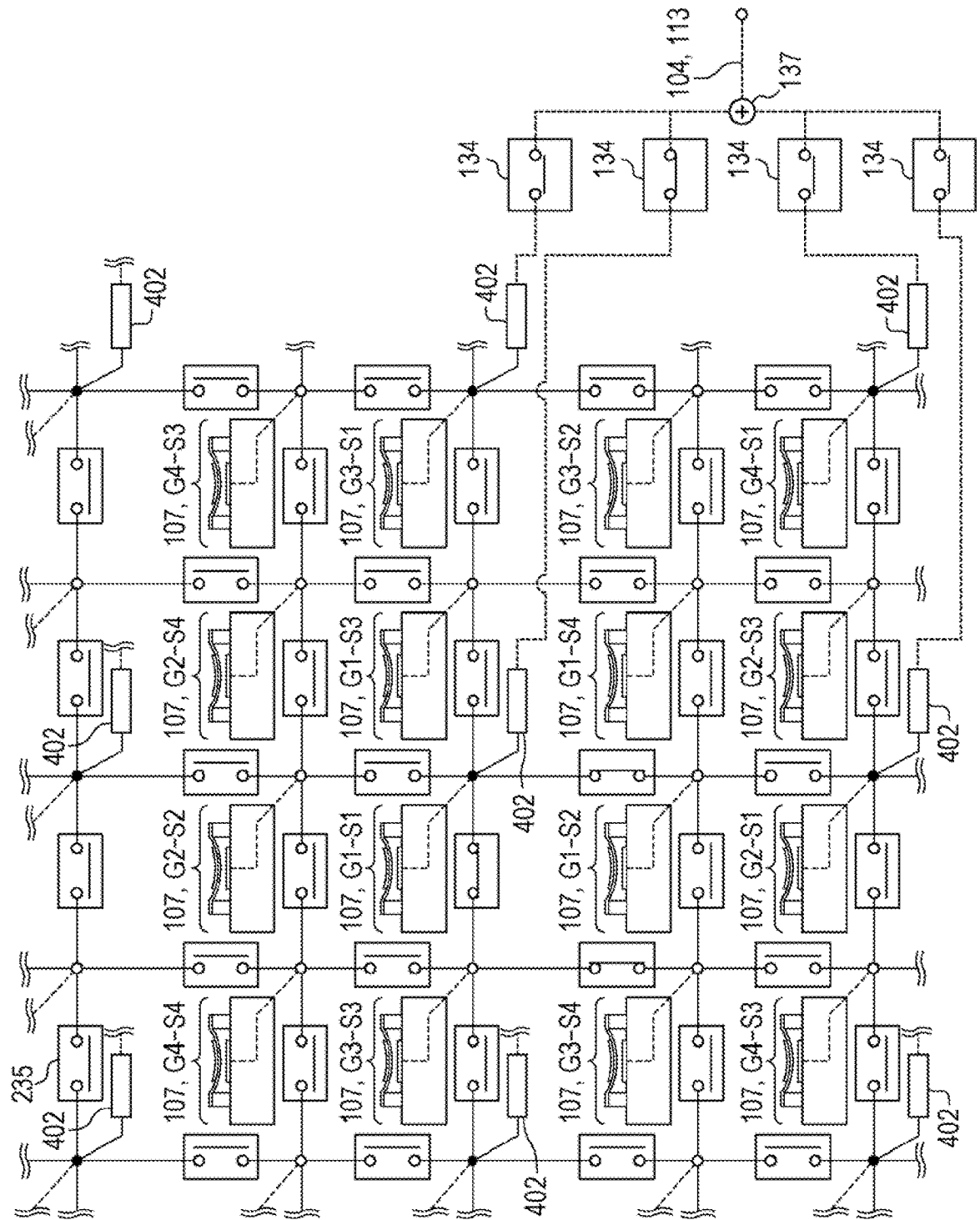

[Fig. 13A]
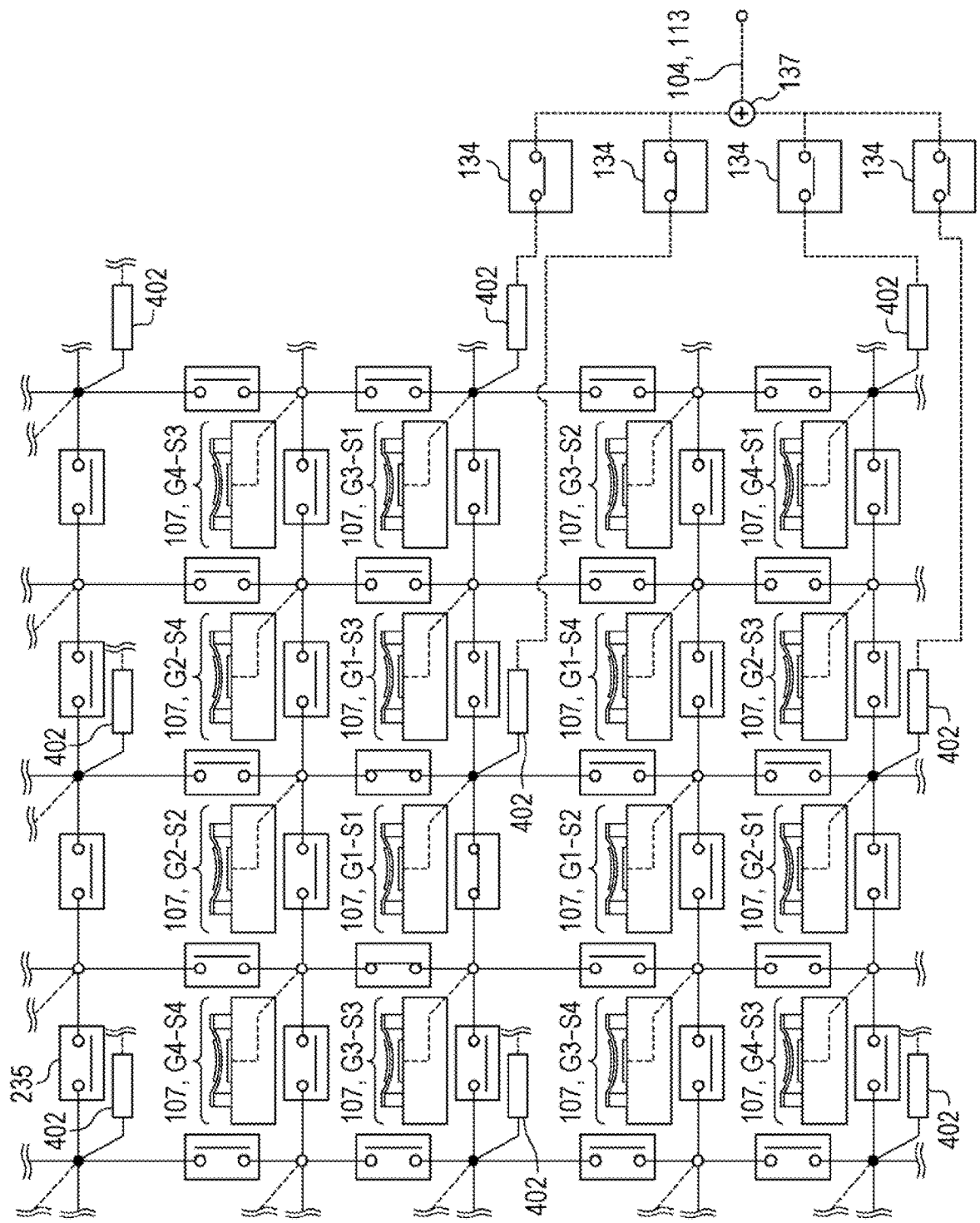

[Fig. 13B]
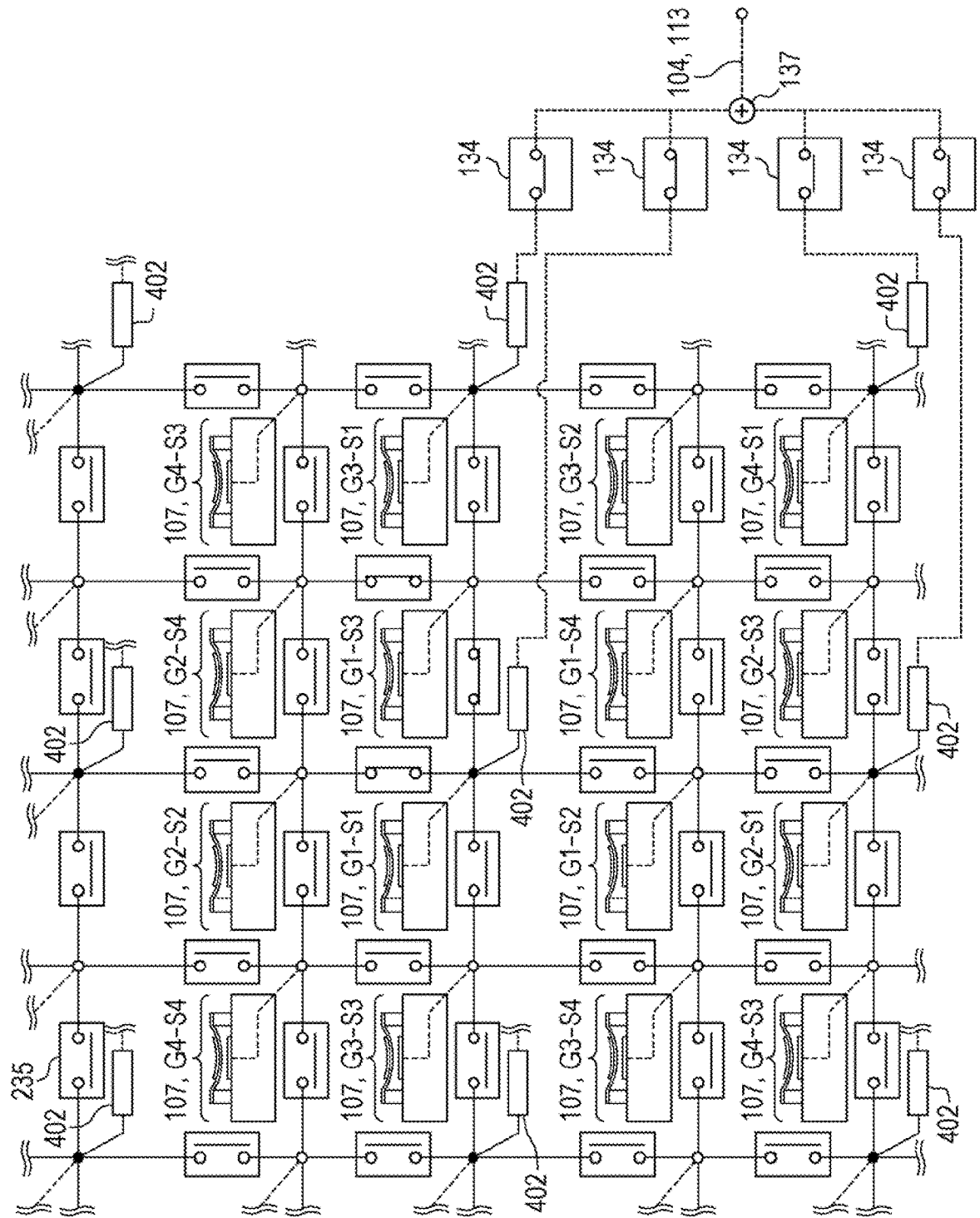

[Fig. 14A]
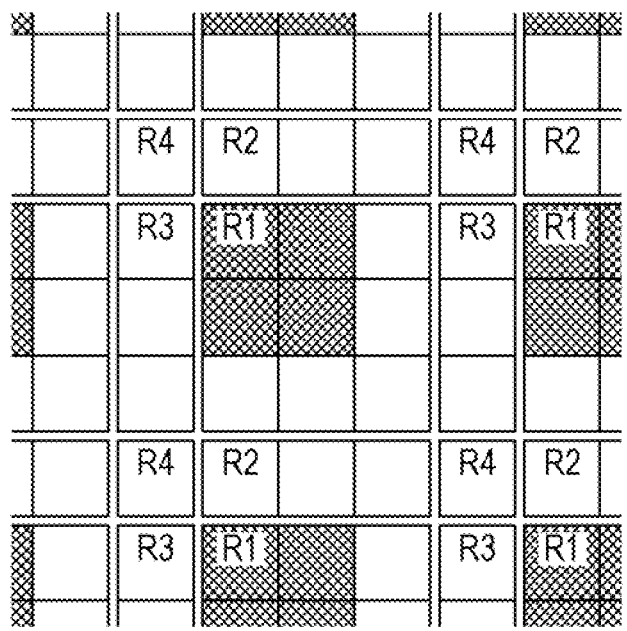
[Fig. 14B]
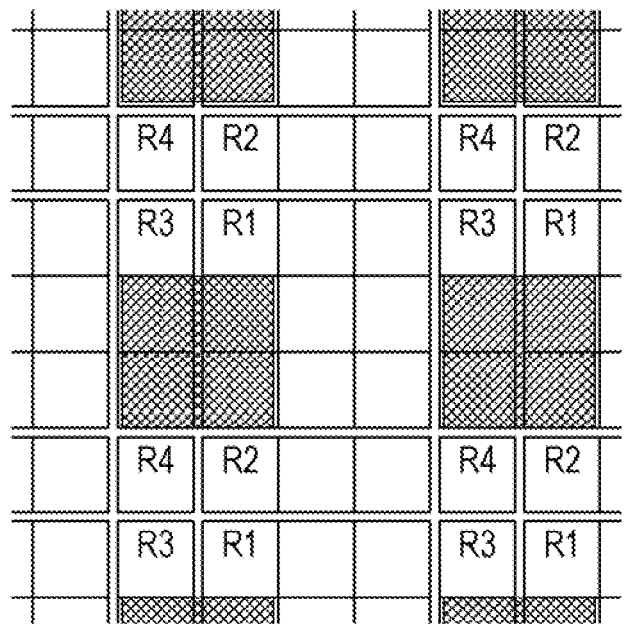

[Fig. 14C]
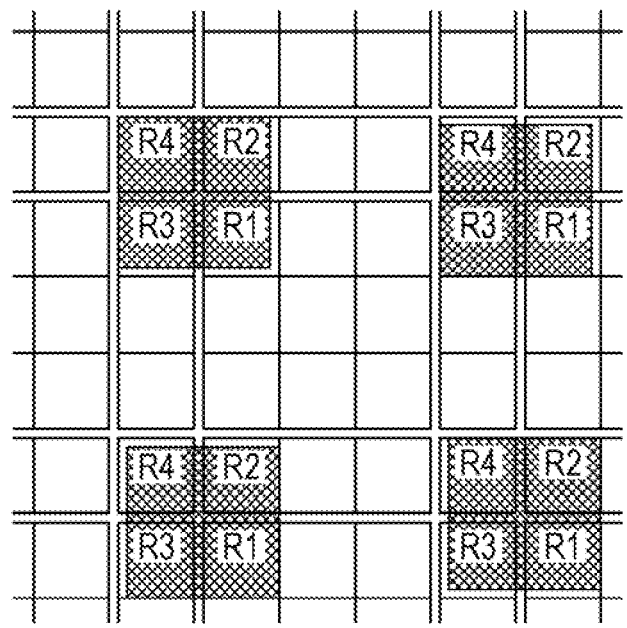
[Fig. 14D]
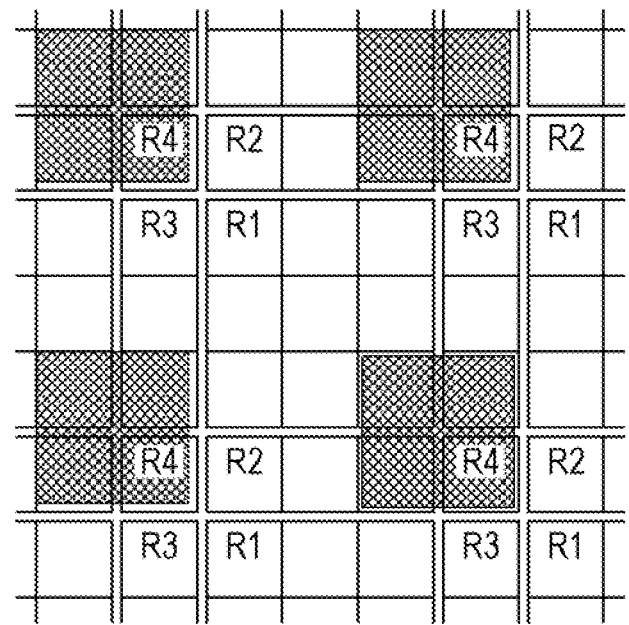

[Fig. 15A]
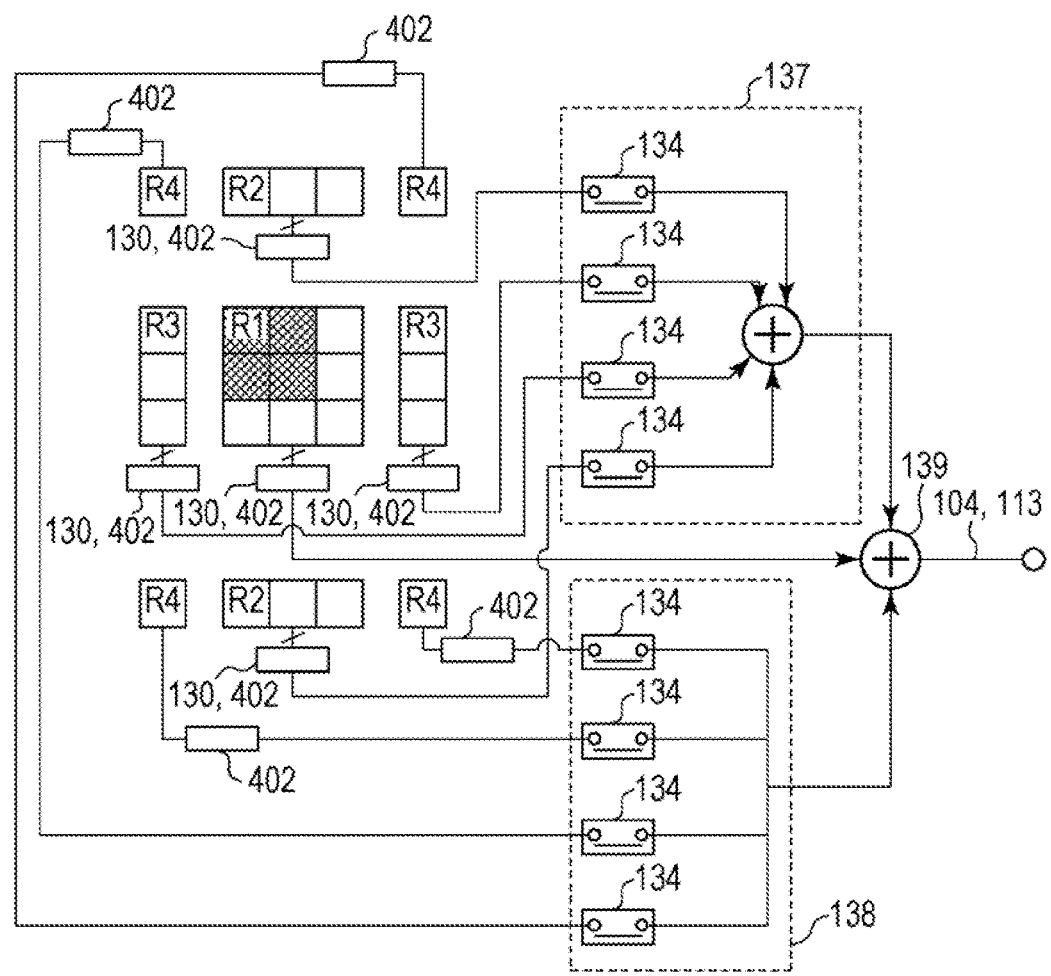

[Fig. 15B]
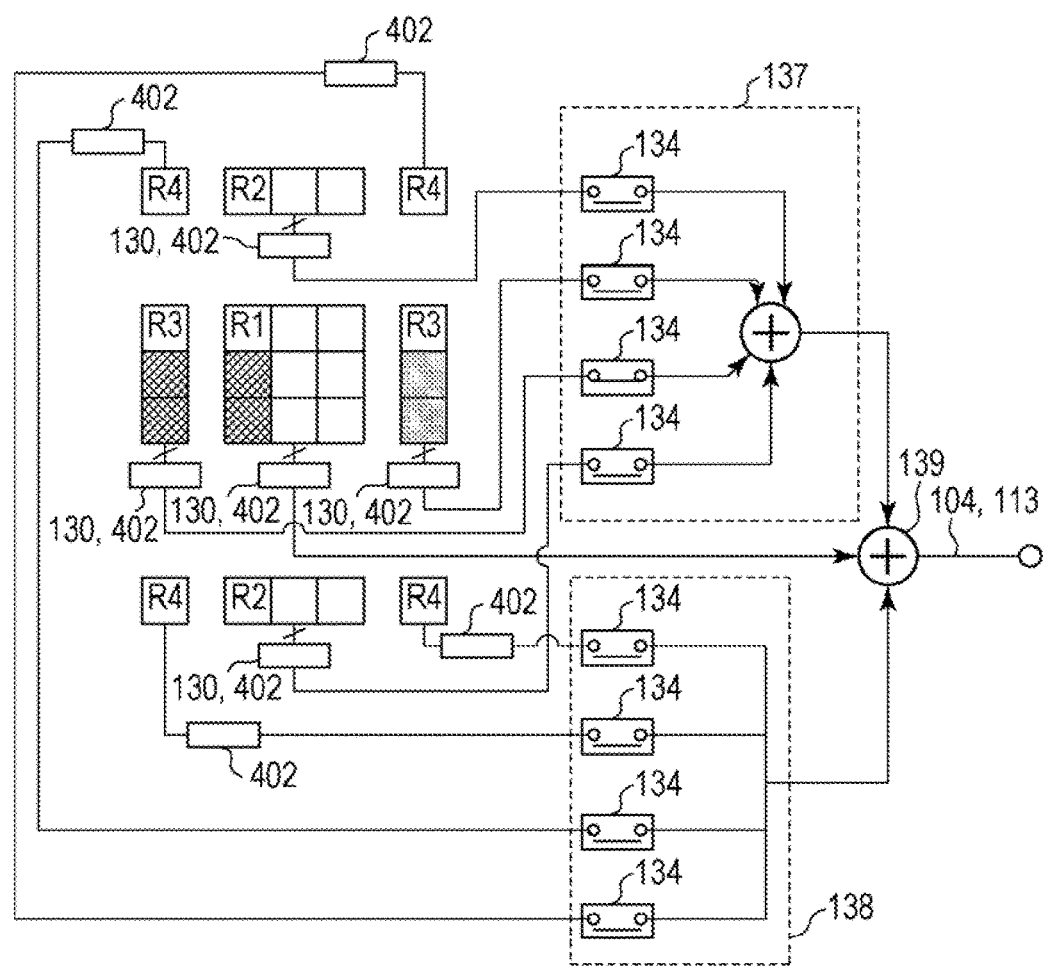

[Fig. 16A]
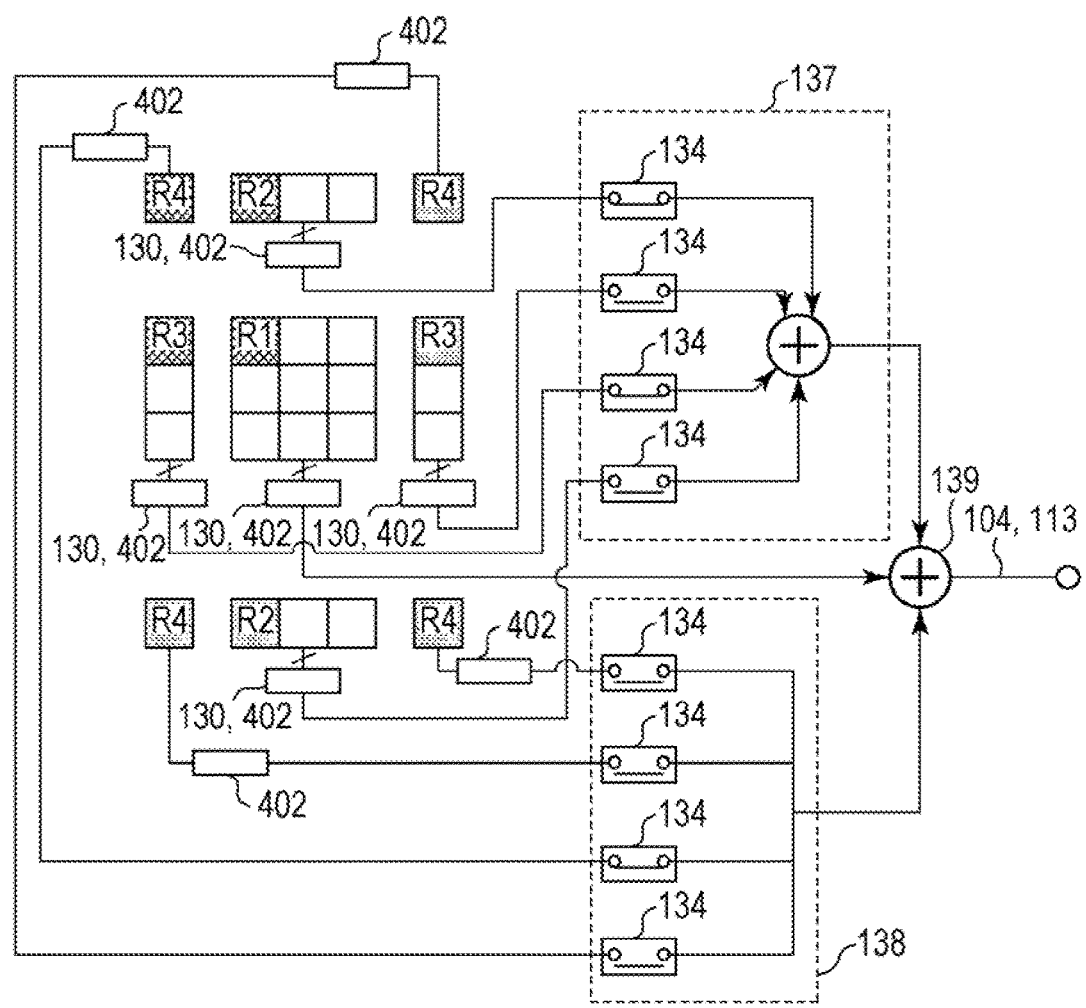

[Fig. 16B]
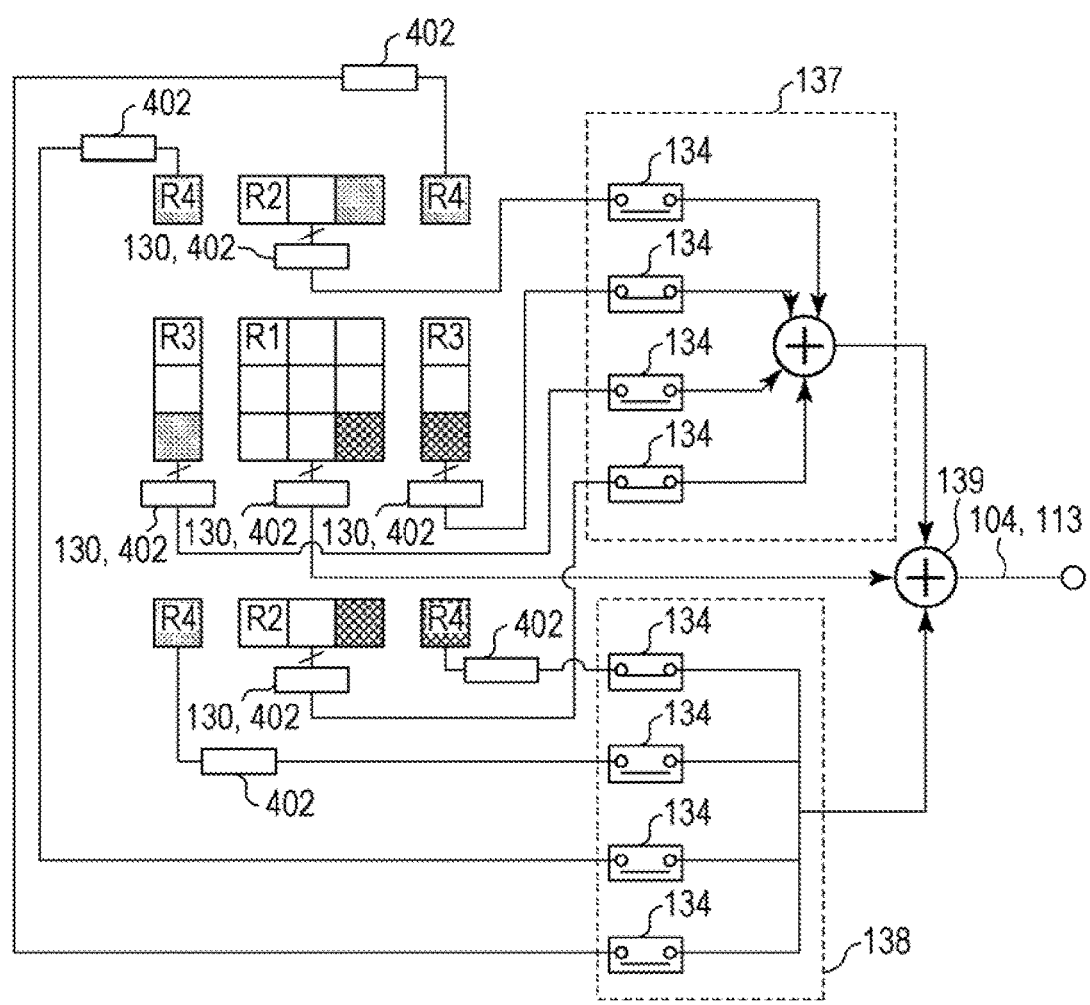

[Fig. 17]
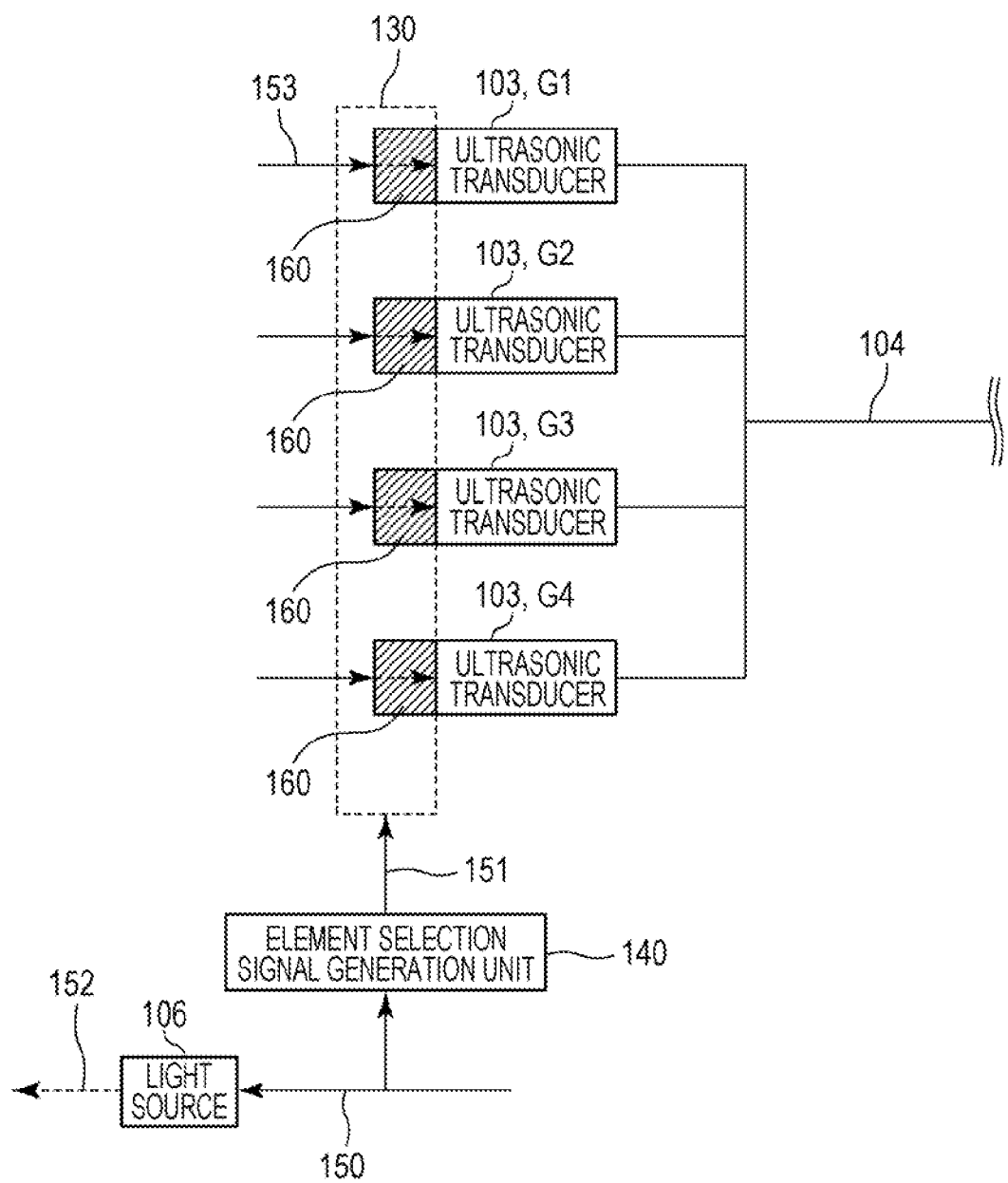

[Fig. 18A]
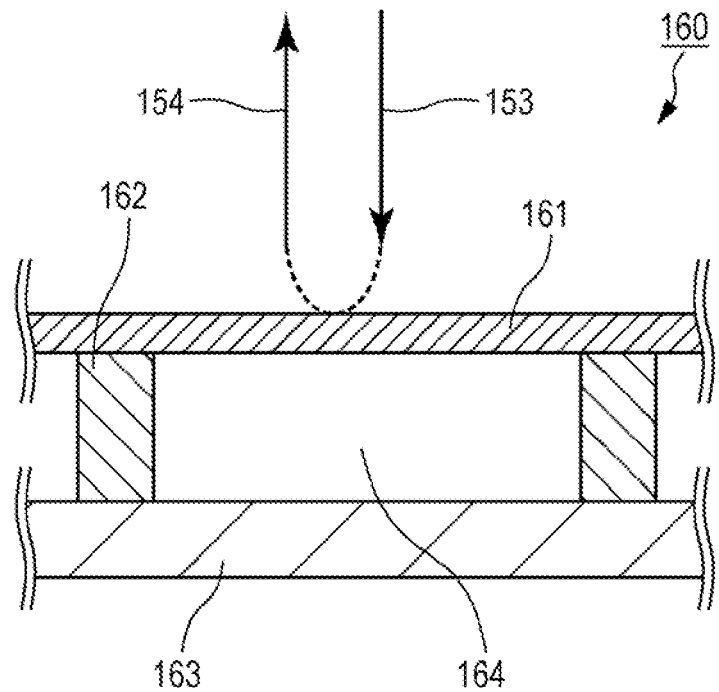
[Fig. 18B]
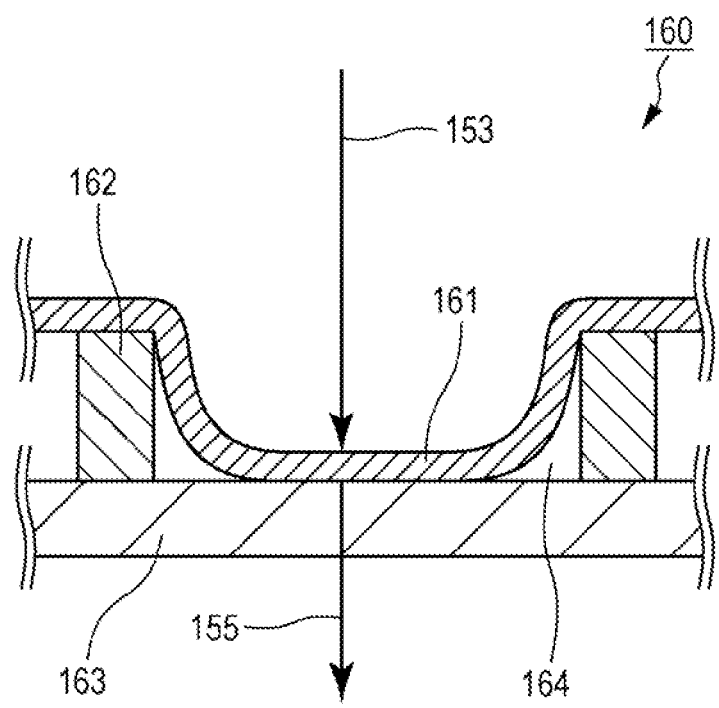

[Fig. 19A]
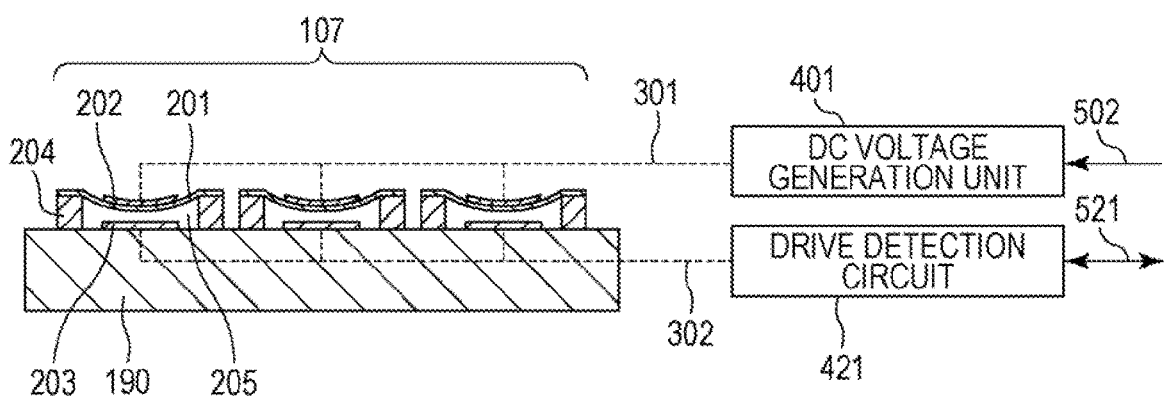
[Fig. 19B]
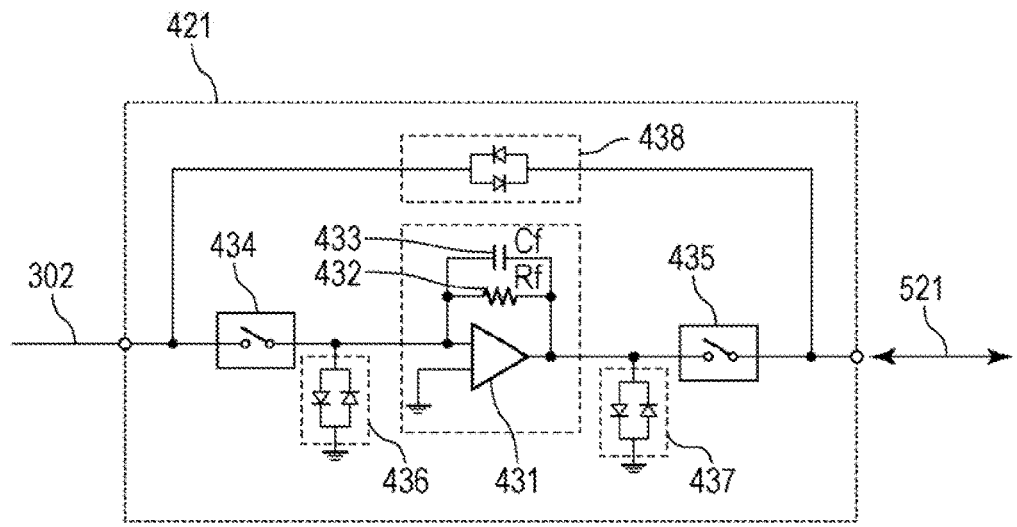

[Fig. 20A]
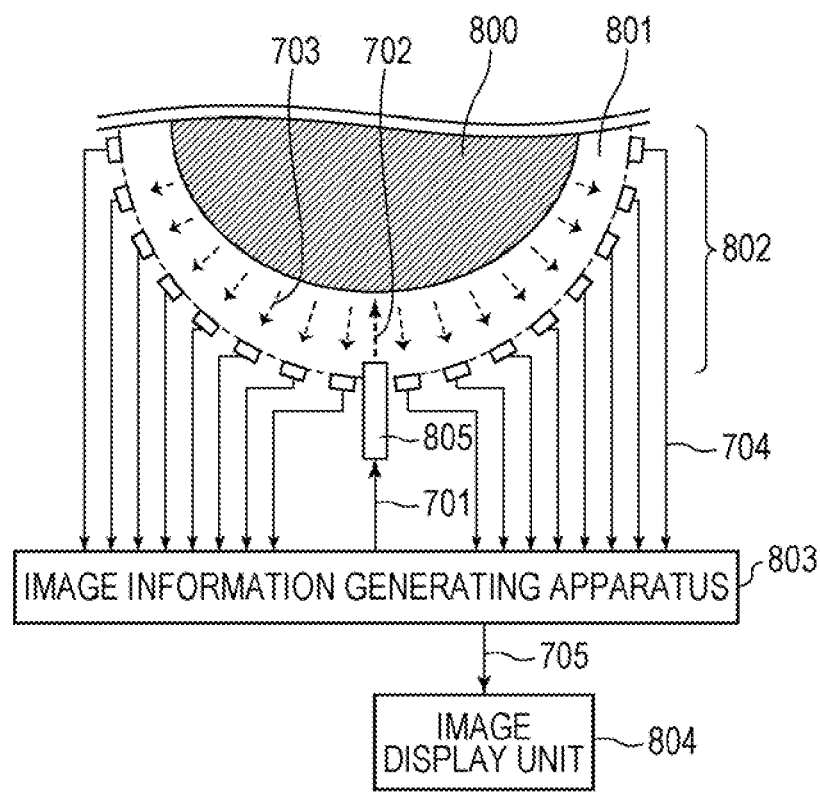
[Fig. 20B]
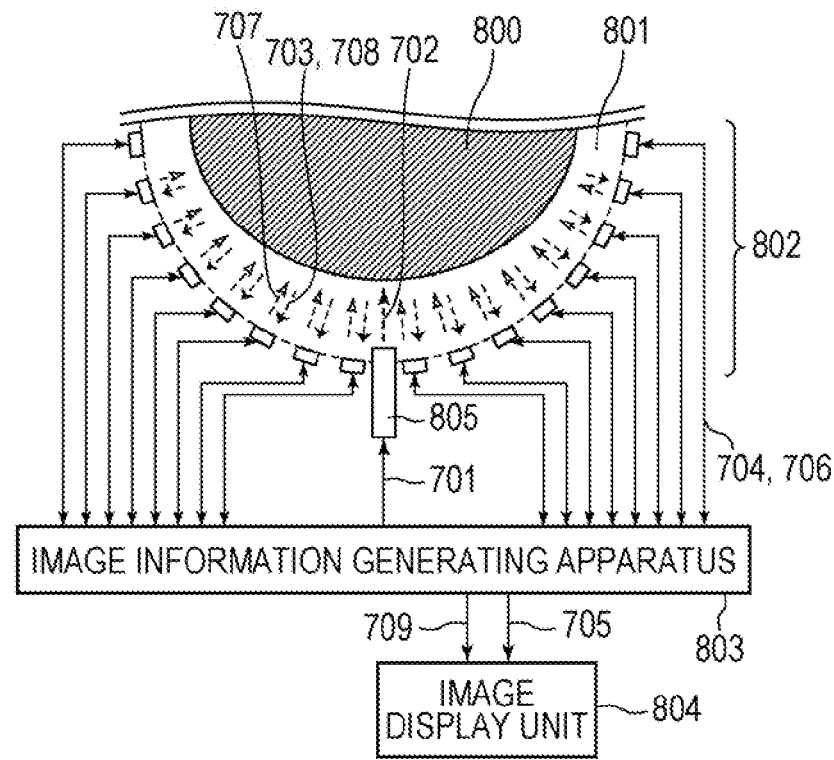

PROBE, TRANSDUCER UNIT, AND SUBJECT INFORMATION ACQUISITION APPARATUS

TECHNICAL FIELD

The present invention relates to a probe capable of receiving a photoacoustic wave by a photoacoustic effect, a transducer unit, and a subject information acquisition apparatus.

BACKGROUND ART

PTL 1 discloses a measurement system in which a subject is irradiated with light, an acoustic wave (which is typically an ultrasonic wave, but is described as a photoaccoustic wave in this specification) is generated from a measurement target in the subject by a photoacoustic effect, and the generated acoustic wave is received using a hemispherical probe. The hemispherical probe is constituted by a plurality of ultrasonic transducers disposed on a hemispheric surface.

This hemispherical probe is described with reference to FIG. 21. In FIG. 21, the reference numeral 10 denotes a subject, 11 denotes a light source, 12 denotes a probe, 13 denotes an ultrasonic transducer, 21 denotes light, 22 denotes photoacoustic waves, and 30 denotes a medium. The hemispherical probe 12 is hemispherical in shape, and is provided with a plurality of ultrasonic transducers 13 and a light source 11. The subject 10 is disposed to be partially surrounded by the hemisphere of the probe 12, the medium 30 is disposed to fill the space between the subject 10 and the probe 12. The subject 10 is irradiated with the light 21 from the light source 11. The photoacoustic waves 22 generated at the subject are received by a plurality of ultrasonic transducers 13 provided in the probe 12 and used for imaging the subject.

CITATION LIST

Patent Literature

PTL 1: U.S. Patent Application Publication No. 2011/0306865

SUMMARY OF INVENTION

Technical Problem

If the distance between adjoining ultrasonic transducers arranged hemispherically is long, there is a possibility that an artifact (i.e. a noise component) which is a virtual image that does not exist occurs in an acquired image of the subject. An exemplary method for reducing occurrence of artifacts may be narrowing the distance between the elements of the ultrasonic transducers.

Narrowing the distance between the elements, however, has the following problem: the number of ultrasonic transducers needs to be increased significantly and the wires connecting with an external apparatus of the probe increase in size, thereby deteriorating operability of the probe.

The present invention provides a probe capable of acquiring subject information, for reducing generation of artifacts without increasing the number of wires connected to the outside.

Solution to Problem

A probe including a plurality of ultrasonic transducers, wherein the ultrasonic transducers are divided into a plurality of groups, two adjoining ultrasonic transducers belong to different groups, and the probe includes a group selection unit configured to switch signals of the ultrasonic transducers to be outputtable for each of the groups.

Further features of the present invention will become apparent from the following description of exemplary embodiments with reference to the attached drawings.

Advantageous Effects of Invention

A probe capable of acquiring subject information, for reducing generation of artifacts without increasing the number of wires connected to the outside can be provided.

BRIEF DESCRIPTION OF DRAWINGS

FIG. 1A schematically illustrates an exemplary photoacoustic probe according to a first embodiment.
FIG. 1B schematically illustrates an exemplary photoacoustic probe according to a first embodiment.
FIG. 1C schematically illustrates an exemplary photoacoustic probe according to a first embodiment.
FIG. 1D schematically illustrates an exemplary photoacoustic probe according to a first embodiment.
FIG. 2A schematically illustrates operations of the photoacoustic probe according to the first embodiment.
FIG. 2B schematically illustrates operations of the photoacoustic probe according to the first embodiment.
FIG. 2C schematically illustrates operations of the photoacoustic probe according to the first embodiment.
FIG. 2D schematically illustrates operations of the photoacoustic probe according to the first embodiment.
FIG. 3A schematically illustrates an exemplary photoacoustic probe according to a second embodiment.
FIG. 3B schematically illustrates an exemplary photoacoustic probe according to a second embodiment.
FIG. 3C schematically illustrates an exemplary photoacoustic probe according to a second embodiment.
FIG. 4A schematically illustrates another example of the photoacoustic probe according to the second embodiment.
FIG. 4B schematically illustrates another example of the photoacoustic probe according to the second embodiment.
FIG. 4C schematically illustrates another example of the photoacoustic probe according to the second embodiment.
FIG. 4D schematically illustrates another example of the photoacoustic probe according to the second embodiment.
FIG. 5A schematically illustrates yet another example of the photoacoustic probe according to the second embodiment.
FIG. 5B schematically illustrates yet another example of the photoacoustic probe according to the second embodiment.
FIG. 5C schematically illustrates yet another example of the photoacoustic probe according to the second embodiment.
FIG. 6A schematically illustrates an exemplary photoacoustic probe according to a third embodiment.
FIG. 6B schematically illustrates an exemplary photoacoustic probe according to a third embodiment.
FIG. 6C schematically illustrates an exemplary photoacoustic probe according to a third embodiment.
FIG. 7A schematically illustrates another example of the photoacoustic probe according to the third embodiment.
FIG. 7B schematically illustrates another example of the photoacoustic probe according to the third embodiment.
FIG. 8A schematically illustrates an exemplary photoacoustic probe according to fourth and fifth embodiments.

FIG. 8B schematically illustrates an exemplary photoacoustic probe according to fourth and fifth embodiments.

FIG. 9A schematically illustrates an exemplary photoacoustic probe according to a sixth embodiment.

FIG. 9B schematically illustrates an exemplary photoacoustic probe according to a sixth embodiment.

FIG. 10A schematically illustrates an exemplary photoacoustic probe according to seventh and eighth embodiments.

FIG. 10B schematically illustrates an exemplary photoacoustic probe according to seventh and eighth embodiments.

FIG. 10C schematically illustrates an exemplary photoacoustic probe according to seventh and eighth embodiments.

FIG. 11A schematically illustrates an exemplary photoacoustic probe according to a ninth embodiment.

FIG. 11B schematically illustrates an exemplary photoacoustic probe according to a ninth embodiment.

FIG. 11C schematically illustrates an exemplary photoacoustic probe according to a ninth embodiment.

FIG. 11D schematically illustrates an exemplary photoacoustic probe according to a ninth embodiment.

FIG. 12A schematically illustrates an exemplary photoacoustic probe according to a tenth embodiment.

FIG. 12B schematically illustrates an exemplary photoacoustic probe according to a tenth embodiment.

FIG. 13A schematically illustrates an exemplary photoacoustic probe according to the tenth embodiment.

FIG. 13B schematically illustrates an exemplary photoacoustic probe according to the tenth embodiment.

FIG. 14A schematically illustrates an exemplary photoacoustic probe according to an eleventh embodiment.

FIG. 14B schematically illustrates an exemplary photoacoustic probe according to an eleventh embodiment.

FIG. 14C schematically illustrates an exemplary photoacoustic probe according to an eleventh embodiment.

FIG. 14D schematically illustrates an exemplary photoacoustic probe according to an eleventh embodiment.

FIG. 15A schematically illustrates an exemplary photoacoustic probe according to the eleventh embodiment.

FIG. 15B schematically illustrates an exemplary photoacoustic probe according to the eleventh embodiment.

FIG. 16A schematically illustrates an exemplary photoacoustic probe according to the eleventh embodiment.

FIG. 16B schematically illustrates an exemplary photoacoustic probe according to the eleventh embodiment.

FIG. 17 schematically illustrates an exemplary photoacoustic probe according to a twelfth embodiment.

FIG. 18A schematically illustrates an exemplary photoacoustic probe according to the twelfth embodiment.

FIG. 18B schematically illustrates an exemplary photoacoustic probe according to the twelfth embodiment.

FIG. 19A schematically illustrates an exemplary subject information acquisition apparatus according to a thirteenth embodiment.

FIG. 19B schematically illustrates an exemplary subject information acquisition apparatus according to a thirteenth embodiment.

FIG. 20A schematically illustrates an exemplary subject information acquisition apparatus according to a fourteenth embodiment.

FIG. 20B schematically illustrates an exemplary subject information acquisition apparatus according to a fifteenth embodiment.

DESCRIPTION OF EMBODIMENTS

Figure 21:
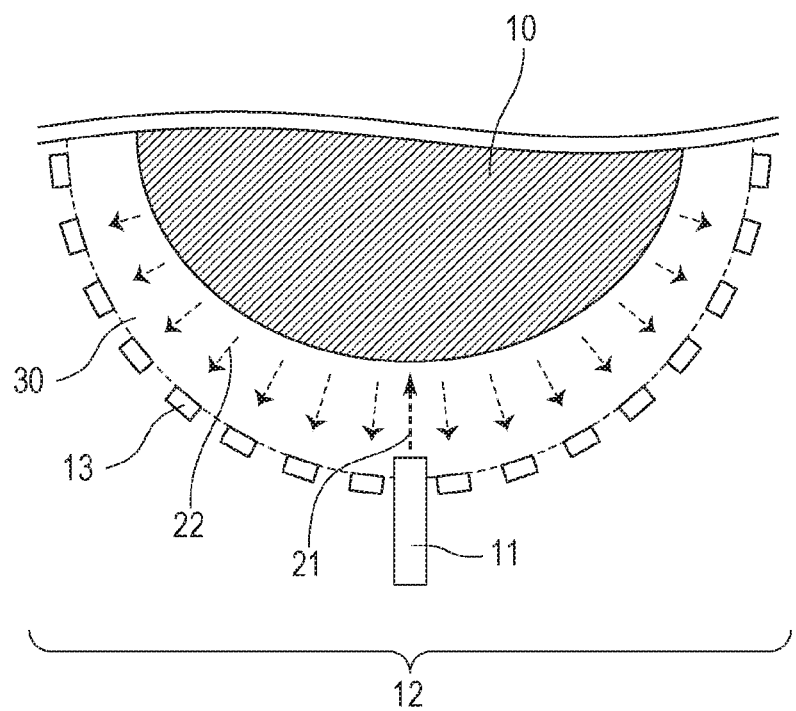
FIG. 21 illustrates a photoacoustic probe of a related art.

Hereinafter, embodiments of the present invention are described with reference to the drawings. It is important in the present embodiment that a plurality of ultrasonic transducers are divided into a plurality of groups, and that a group selection unit is provided to switch signals of the ultrasonic transducers to be outputtable for each group corresponding to light-emitting timing of a light source.

Hereinafter, the present invention is described with reference to various embodiments. Regarding the constituents of the photoacoustic probe of the present invention, components indicating the same parts are denoted by the same reference numerals throughout the drawings and are not described, if not necessary, for each drawing.

First Embodiment

FIGS. 1A to 1D schematically illustrate a photoacoustic probe of the present embodiment. In FIGS. 1A to 1D, the reference numeral 100 denotes a photoacoustic probe, 101 collectively denotes a plurality of ultrasonic transducer disposed portion, 102 denotes a housing, 103 denotes an ultrasonic transducer, 104 denotes a cable, 106 denotes a light source, 130 denotes a group selection unit, 140 denotes an element selection signal generating unit, 150 denotes a synchronization signal of the light source, and 151 denotes an element selection signal. The ultrasonic transducer disposed portion 101 represents an inner portion of the housing 102, and has a curved surface shape depressed as a bowl. FIG. 1A schematically illustrates a photoacoustic probe of the present embodiment. In the photoacoustic probe of the present embodiment, a plurality of ultrasonic transducers 103 are arranged hemispherically at positions to face the subject. The photoacoustic wave received by each ultrasonic transducer 103 is output, via a cable 104 having a plurality of signal lines, to an external apparatus (not illustrated) connected by a connector. Portions of the hemispherically arranged ultrasonic transducers 103 arranged not to face the subject, connection wiring portion with the cable 104, and the group selection unit 130 are covered with the housing 102. The element selection signal generating unit 140 may be disposed in the housing 102 or may be provided in an unillustrated external device.

The ultrasonic transducer 103 may be any transducer that can receive a photoacoustic wave (i.e., an ultrasonic wave): if a piezoelectric transducer and the like is used, configuration thereof becomes easily.

FIG. 1B is a top view of the photoacoustic probe seen from the subject side. A plurality of ultrasonic transducers 103 are disposed on the hemispherical surface of the photoacoustic probe 100 (hereafter, referred to as a hemispheric surface) facing the subject. In the present invention, the plurality of ultrasonic transducers 103 are divided into a plurality of groups. The ultrasonic transducers 103 belonging to a first group are denoted by G1, the ultrasonic transducers 103 belonging to a second group are denoted by G2, the ultrasonic transducers 103 belonging to a third group are denoted by G3, and the ultrasonic transducers 103 belonging to a fourth group are denoted by G4.

The light source 106 is disposed at the center of the hemisphere in a manner that light is applied to the subject. The light source 106 may be formed by using solid state laser, semiconductor laser, LED, or an optical fiber that transmits light from these light sources.

FIG. 1C schematically illustrates a partial area of the hemispheric surface on which the plurality of ultrasonic transducers 103 are disposed. In the present embodiment, the ultrasonic transducers 103 belonging to the four groups are arranged at about the same density locally on the hemispheric surface of the photoacoustic probe. Specifically, it is characteristic that the distance from one ultrasonic transducer 103 belonging to the first group to each of the closest ultrasonic transducers 103 belonging to other three groups is substantially the same. That is, the distance between the closest ultrasonic transducers belonging to a plurality of groups is substantially the same for each group.

Since wires connecting to the ultrasonic transducers 103 belonging to the tour groups can be disposed adjacently, one ultrasonic transducer 103 belonging to one group among a plurality of groups can be selected easily.

The density of the ultrasonic transducers 103 is the same when any of the groups is selected. Therefore, an image of a subject does not locally deteriorate even if the subject moves slightly while a plurality of groups are selected and the signals are taken from all the ultrasonic transducers. The ultrasonic transducers 103 belonging to the same group are disposed not to adjoin each other, and two adjoining transducers 103 belong to different groups. That is, an ultrasonic transducer belonging to first group is disposed between ultrasonic transducers 103 belonging to second group. A distance between two ultrasonic transducers 103 belonging to different groups is smaller than a distance between two ultrasonic transducers 103 belonging to the same group. One ultrasonic transducer 103 is surrounded by ultrasonic transducers 103 belonging to groups different from that of the ultrasonic transducer 103. For example, as illustrated in FIG. 1C, the ultrasonic transducer 103 belonging to the first group (G1) is surrounded by the ultrasonic transducer 103 belonging to the second group (G2), the ultrasonic transducer 103 belonging to the third group (G3), and the ultrasonic transducer 103 belonging to the fourth group (G4). Further, the ultrasonic transducers 103 surrounding the ultrasonic transducer 103 belonging to the first group (G1) are selected in substantially the same number from each of the different groups.

FIG. 1D schematically illustrates the ultrasonic transducers 103 belonging to the four groups and signals output from the cable 104 of the photoacoustic probe 100. A light source synchronization signal 150 in synchronization with light-emitting timing of the light source 106 is input in the element selection signal generating unit 140. Each time the input light source synchronization signal 150 is input in the element selection signal generating unit 140, the element selection signal generating unit 140 generates the element selection signal 151.

The element selection signal 151 is generated in a manner such that the groups to be selected are changed sequentially. In response to the element selection signal 150, the group selection unit 130 can switch the signal received at the ultrasonic transducer 103 belonging to the selected group to be output from the cable 104. In FIG. 1D, the reference numeral 152 denotes exit light from the light source 106.

Next, an operation of the group selection unit 130 is described with reference to FIGS. 2A to 2D. First, suppose that the element selection signal 151 is now selecting the first group G1. In this state, as illustrated in FIG. 2A, the signal output from the cable 104 is a signal 901 received by the ultrasonic transducer 103 belonging to the first group G1. Then, according to timing at which the light source 106 emits light, the state is changed into a state where the element selection signal 151 is selecting the second group G2. In this state, as illustrated in FIG. 2B, the signal output from the cable 104 is a signal 902 received by the ultrasonic transducer 103 belonging to the second group G2.

Thereafter, each time the light source 106 emits light, the element selection signal 151 changes its state to select the third group G3 and then the fourth group G4. Accordingly, the signal output from the cable 104 is changed sequentially, as illustrated in FIG. 2C, into a signal 903 received by the ultrasonic transducer 103 belonging to the third group G3, and then as illustrated in FIG. 2D, into a signal 904 received by the ultrasonic transducer 103 belonging to the fourth group G4.

At timing at which the light source 106 emits light the 4th time, the element selection signal 151 returns to the state in which it is selecting the first group G1, and the signal output from the cable 104 is the signal 901 received by the ultrasonic transducer 103 belonging to the first group G1.

As described above, corresponding to the timing at which the light source 106 emits light, the group to which the ultrasonic transducer 103 outputting the received signal belongs changes in the order of FIGS. 2A, 2B, 2C, 2D, and 2A. Therefore, in the present embodiment, while the light source emits light four times, the photoacoustic waves from the subject can be received from all the ultrasonic transducers 103 provided in the photoacoustic probe 100 and can be taken out of the photoacoustic probe. The distance between the ultrasonic transducers 103 can be narrowed effectually by using all the signals from the four groups during image reconstruction.

Therefore, the photoacoustic signals from the subject to reduce the generation of artifacts as much as possible can be acquired.

Further, in the present embodiment, since the reception signals from the ultrasonic transducer 103 are taken out at several times, the number of wires of the cable 104 for connecting with the outside remains small even if the number of the ultrasonic transducers 103 is increased. Therefore, the diameter of the cable can be increased and a decrease in operability is reduced. According to the present embodiment, a photoacoustic probe capable of acquiring subject information, for reducing generation of artifacts without increasing the number of wires connected to output signals outside can be provided.

Although a configuration including four groups is described in this specification, the number of groups is not limited to the same: the number is suitably determined depending for example on the characteristic of the photoacoustic probe to be obtained.

The number of groups can be arbitrarily determined depending on the size of the element of the ultrasonic transducer 103, the distance between the elements, and frequency at which artifact occurs.

Second Embodiment

In a second embodiment, a shape of a surface on which a plurality of ultrasonic transducers 103 are disposed is described. Other configurations are the same as those of the first embodiment. FIG. 3A schematically illustrates a photoacoustic probe according to the present embodiment.

The present embodiment is characterized by that, as illustrated in FIG. 3B, a plurality of ultrasonic transducers 103 are disposed on polygonal planes, and a plurality of polygonal planes constitute a pseudo-hemispheric recess.

With the configuration of the present embodiment, a plurality of ultrasonic transducers 103 in the photoacoustic probe 100 can be disposed to face the vicinity of an arbitrary point in the ultrasonic transducer disposed portion 101. Therefore, a function substantially equivalent to that of the configuration, described in the related art, in which a plurality of ultrasonic transducers 103 are disposed on a hemispheric surface can be achieved.

Since the same function is achieved with a very simple configuration compared with the configuration in which a plurality of ultrasonic transducers 103 are disposed on a hemispheric surface, the production man-hours of the photoacoustic probe and the size of the photoacoustic probe can be reduced.

The ultrasonic transducer disposed portion 101 of the present embodiment is characterized by that the recess is formed by a polyhedron with a plurality of planes combined, and one wire connected to the elements is drawn out from each of the plurality of planes.

The present embodiment is described with reference to a schematic diagram of FIG. 3B in the state where the housing 102 of the photoacoustic probe of the present invention is removed. In FIG. 3B, the reference numeral 110 denotes the ultrasonic transducer unit, 120 denotes a frame, and 106 denotes a light source. In the present embodiment, each of the polyhedra provided in the ultrasonic transducer disposed portion 101 in the photoacoustic probe 100 is constituted by a plurality of ultrasonic transducer units 110.

A plurality of ultrasonic transducer units 110 are held by the frame 120 in a manner such that the planes on which the ultrasonic transducers 103 are disposed form a polyhedron. The ultrasonic transducer unit 110 has a hole or is deformed partially for disposing the light source 106 at the portion at which the light source 106 is disposed.

FIG. 3C schematically illustrates cross sections of the ultrasonic transducer units 110. The ultrasonic transducer unit 110 has a planar polygonal shape, and is equipped with a plurality of ultrasonic transducers 103 on one of the faces (i.e., the side that constitutes the recess). Here, the recess constitutes a photoacoustic wave receiving unit of the photoacoustic wave.

A subcable 113 is drawn to the outside at the center of the other side (i.e., the back side). No parts are disposed at the peripheral portion on the back side. The peripheral portion on the back side has a shape corresponding to the front side of the corresponding frame 120. When joined together, surfaces of the peripheral portion and the frame 120 are in contact with each other with no space therebetween.

The frame 120 has openings 121 at the center of the region at which the ultrasonic transducer units 110 are disposed. The subcable 113 of the ultrasonic transducer unit 110 is drawn out of the frame 120 through the opening 121. Since the frame 120 has the openings 121, the frame 120 can both ultrasonic transducer units 110 and draw the subcables 113 from the ultrasonic transducer units 110.

As illustrated in FIG. 3B, a plurality of subcables 113 connected to a plurality of ultrasonic transducer units 110 are assembled into a bunch which is connected with the outside of the photoacoustic probe as a cable 104 of the photoacoustic probe 100.

FIGS. 4A to 4D and 5A to 5C schematically illustrate a configuration of the polyhedron of the photoacoustic probe according to the present embodiment. First, in the example of FIGS. 4A and 4B, the recess is constituted by the ultrasonic transducer units 110, which are eight equilateral triangles 114 of the same size. One edge of the equilateral triangle is disposed to be perpendicular to the depth of the recess at the deepest portion of the recess. FIG. 4A schematically illustrates the surfaces of the ultrasonic transducer disposed portion 101 has. FIG. 4B is a schematic plan view of a disposing surface of the ultrasonic transducer disposed portion 101 seen from the subject side. The dotted line in FIG. 4B represents the outer shape of the photoacoustic probe 100.

This shape is the same as that of the surface of the object when divided a regular icosahedron into half. According to the present embodiment, since the photoacoustic wave generated at the subject is received by the ultrasonic transducers 103 disposed on an octahedron, information closer to that of the configuration in which the ultrasonic transducers 103 are disposed on the hemispherical (curved) surface can be acquired.

Since the octahedron can be constituted by three kinds of ultrasonic transducer units 110, a polyhedron with a greater number of planes can be obtained efficiently by combining fewer kinds of ultrasonic transducer units 110. Another form of the present embodiment is described with reference to FIG. 4C. This form is characterized by being constituted by line symmetrical right-angled triangles 116A and 116B each having angles of 60° and 30°.

As illustrated in FIG. 4C, the line symmetrical right-angled triangles 116A and 116B are disposed horizontally to form an equilateral triangle. Therefore, the polyhedron illustrated in FIGS. 4A and 4B can be implemented by using eight of each of the two kinds of right-angled triangles 116A and 116B illustrated in FIG. 4C.

Since an octahedron illustrated in FIGS. 4A and 4B can be constituted only by the ultrasonic transducer units 110 of two kinds of symmetrical right-angled triangles 116A and 116B illustrated in FIG. 4C, the ultrasonic transducer units 110 can be fabricated in common. Therefore, a photoacoustic probe with high fabrication efficiency can be provided.

Since the ultrasonic transducer units 110 of the same shape are used, even if a malfunction occurs in the element, load in replacement of the ultrasonic transducer units 110 is small.

In the present embodiment, if more information on the photoacoustic wave to acquire is needed, as illustrated in FIG. 4D, a form in which a polyhedron is constituted by a total of 12 triangles; eight right-angled triangles of the same size, and four equilateral triangles of half the size of the right-angled triangle.

Since a dodecahedron can be formed in this manner, the photoacoustic waves generated at the subject can be acquired from further more directions.

Another form of the present embodiment is described with reference to FIGS. 5A to 5C. This form is characterized by that a recess is formed using 28 isosceles triangles 115 as illustrated in FIGS. 5A and 5B.

An outer shape of the ultrasonic transducer unit 110 of the present embodiment is an isosceles triangle 115, of which edge ratio is 6:6:(9−√5), vertex angle is 68.62°, and two base angles are each 55.69°.

The base edge of the isosceles triangle is disposed to be perpendicular to the depth of the recess at the deepest portion of the recess. This shape is the same as that of the surface of the object when divided a pentakis dodecahedron into half.

According to the present embodiment, since the photoacoustic wave generated at the subject is received by the ultrasonic transducers 103 disposed on an icosaoctahedron, information very close to that of the configuration in which the ultrasonic transducers 103 are disposed on the hemispherical surface can be acquired.

Since the icosaoctahedron can be constituted by a kind of ultrasonic transducer unit 110, a polyhedron with a greater number of planes can be obtained very efficiently by combining fewer kinds of ultrasonic transducer units 110.

In the present embodiment, since a plurality of ultrasonic transducers 103 can be disposed using a single ultrasonic transducer unit 110 in a substantially the same manner as in a case where the ultrasonic transducers are disposed on the hemispheric surface, a photoacoustic probe of a simple configuration capable of acquiring detailed information on the photoacoustic wave from a subject can be provided.

In the present embodiment, if more information on the photoacoustic wave to acquire is needed, as illustrated in FIG. 5C, a form in which a polyhedron is constituted by a total of 32 triangles: 28 isosceles triangle of the same size and four right-angled triangles 117A and 117B of half the size of the isosceles triangles. Since an icosadodecahedron can be formed in this manner, the photoacoustic waves generated at the subject can be acquired from further more directions.

The present invention is not limited to the polyhedra illustrated in FIGS. 4A to 4D and 5A to 5C: any configurations in which a recess is formed by polyhedra can be used in consideration of characteristics to be obtained.

In the present embodiment, the ultrasonic transducers 103 are disposed on the plane and the group selection unit is provided for each ultrasonic transducer unit 110 including the plane. Therefore, a photoacoustic probe of which number of wires drawn from the ultrasonic transducer units 110 can be made minimum, having high cable flexibility, and high operability can be provided.

Further, information substantially equivalent to that of the photoacoustic probe in which the ultrasonic transducers 103 are disposed hemispherically can be acquired by combining a plurality of ultrasonic transducer units 110. Therefore, compared with a configuration in which elements are selected about the ultrasonic transducers disposed on the hemispherical surface, wiring to the group selection unit and arrangement of the circuit unit are easier.

Third Embodiment

In a third embodiment, the ultrasonic transducer 103 is described. Other configurations are the same as those of the second and other embodiments. The ultrasonic transducer of the present embodiment is characterized by using a capacitive micro-machined ultrasonic transducer (hereafter, CMUT) 107. The CMUT is fabricated on, for example, a silicon chip, using a micro electro mechanical systems (MEMS) process to which a semiconductor process is applied.

First, the CMUT 107 is described. The CMUT 107 is constituted by a plurality of cells. FIG. 6A schematically illustrates one of the cells included in the CMUT 107. In FIGS. 6A to 6C, the reference numeral 190 denotes a chip (i.e., a substrate), 201 denotes a vibration film, 202 denotes a first electrode, 203 denotes a second electrode, 204 denotes a support portion, 205 denotes a cavity, 301 denotes a first wire, 302 denotes a second wire, 401 denotes a DC voltage generation unit (i.e., a DC voltage application unit), and 402 denotes a receiving circuit.

The vibration film 201 is supported on the chip 190 by the support portion 204, and vibrates in response to the ultrasonic wave. The first electrode 202 is disposed on the vibration film 201, and the second electrode 203 is disposed on the chip 190 to face the first electrode 202. A set of the first electrode 202 and the second electrode 203 disposed to face each other via the vibration film 201 and the cavity 205 is referred to as a cell 200. That is, a cell of which vibration film including one electrode of a pair of electrodes formed via the cavity is supported vibratable is formed.

The first electrode 202 is drawn out of the chip 190 via the first wire 301 and is connected to the DC voltage generating unit 401, and the second electrode 203 is drawn out of the chip 190 via the second wire 302 and is connected to the receiving circuit 402. That is, one of the pair of electrodes is connected to the DC voltage generating unit 401 and the other is connected to the receiving circuit 402.

The DC voltage generating unit 401 causes several tens to several hundred volts of potential difference between the first electrode 202 and the second electrode 203. When the vibration film 201 and the first electrode 202 vibrate, the distance between the first electrode 202 and the second electrode 203 changes, whereby electrostatic capacity between the electrodes changes. The potential difference between the electrodes causes a microcurrent corresponding to capacity variation. The microcurrent is converted into a voltage from a current by the receiving circuit 402 connected to the second electrode 203, and is then output. Although the first electrode 202 is disposed on the vibration film 201 and the second electrode 203 is disposed on the chip 190 herein, the second electrode 203 may be disposed on the vibration film 201 and the first electrode 202 may be disposed on the chip 190.

FIG. 6B schematically illustrates the chip 190 seen from the side on which the CMUT 107 is formed. FIG. 6B illustrates the outer shapes of the second electrode 203 and the cell 200. A plurality of CMUTs 107 are disposed on the chip 190. A group of cells 200 of which second electrodes 203 are connected to the same receiving circuit 402 functions as an independent photoacoustic wave receiving element (here, the unit of the photoacoustic wave receiving element is referred to as an element).

The reference numeral 208 denotes a wire for connecting in common a plurality of second electrodes 203 in the element constituted by a plurality of cells 200 and taking signals out.

The size of the photoacoustic wave receiving element is in the range of several hundreds of micrometers to several millimeters, and the number of cells 200 in the photoacoustic wave receiving element is in the range of one hundred to several thousands.

FIG. 6C is a circuit diagram of the receiving circuit 402 illustrated in FIG. 6A. In FIG. 6C, the reference numeral 411 denotes an operational amplifier, 412 denotes a feedback resister, 413 denotes feedback capacitance, 414 denotes resistance for offset removal, and 415 denotes capacitance for offset removal.

FIGS. 7A and 7B schematically illustrate the ultrasonic transducer unit 110 according to the present embodiment. In FIGS. 7A and 7B, the reference numeral 107 denotes a CMUT, 220 denotes an interposer, 230 denotes a connector, and 250 denotes a frame.

As illustrated in FIG. 7A, the chip 190 in which a plurality of CMUTs 107 are disposed is held by the interposer 220. The chip 190 is common to a plurality of CMUTs 107. Wires on the chip 190 and the wires on the interposer 220 are electrically connected by a bonding wire 211. The interposer 220 holding the chip 190 includes a patterned thin electrode layer on the front and back sides thereof, and has vias (not illustrated) through which the front and back sides are electrically connectable. With this configuration, the wires connected to the electrodes 202 and 203 on the chip 190 can be electrically connected with the wires on the back side of the interposer 220.

On the back side of the interposer 220, the receiving circuit 402 for receiving signals in the CMUTs 107, and the connector 230 for connecting with the subcable 113 are provided. The second electrode 203 on the chip 190 is connected with the receiving circuit 402 via the interposer 220, and the output of the receiving circuit 402 is connected to the outside via the connector 230 and the subcable 113. The first electrode 202 on the chip 190 is connected with the DC voltage generating, unit 401 via the interposer 220.

The interposer 220 is desirably finned by a member in which glass epoxy is laminated. In this configuration, by using the fabrication method of the circuit board, wiring can be easily formed on a surface and inside of the interposer 220, vias can be easily formed inside the interposer 220. Since more complicated wiring can be formed inside the interposer 220, a wiring layout with smaller parasitic capacitance at the wiring portion can be provided. Therefore, an ultrasonic transducer excellent in receiving characteristics can be provided.

In an interposer 220 using glass epoxy, the receiving circuit 402 can be soldered directly on the interposer. Therefore, since electric reliability with the receiving circuit 402 is high, the receiving circuit 402 can be disposed by a simple method.

The member in which glass epoxy is laminated can attenuate an ultrasonic wave of specific frequency. Therefore, it can be reduced that the photoacoustic wave (i.e., the ultrasonic wave) arrived at the ultrasonic transducer unit 110 enters the interposer, reflects on the back side of the interposer 220, and is superimposed on reception signals as noise.

The interposer 220 is held by the frame 250. The frame 250 has a recess conforming to the shape of the interposer 220, and holds the interposer 220 by dropping into the recess of the frame 250. The frame 250 includes the receiving circuit 402 and the connector 230 on the back side of the interposer 220, and includes an opening at the portion at which the subcable 113 is disposed. A peripheral portion of the frame 250 is shaped to be joined with the frame 120 with no space there between. The frame 250 can be processed into a necessary shape, and can be formed by any materials that provide necessary intensity, such as metal and resin.

The CMUT 107 used in the present embodiment is characterized by having higher responsiveness upon reception of the ultrasonic waves and has a wider frequency bandwidth compared with piezo ultrasonic transducers currently used widely. However, since the CMUT 107 is a current output type element, its receiving characteristic easily deteriorates depending on the capacitance parasitic in wiring.

In the present embodiment, the interposer 220 holding the chip 190 provided with the CMUTs 107 includes the receiving circuit 402 on the back side thereof. Therefore, the wire length from the second electrode 203 to the receiving circuit 402 can be shortened, and capacitance parasitic in the wire can be reduced. Therefore, when the present embodiment is used, an ultrasonic transducer with a wide bandwidth of receiving frequency and with excellent receiving characteristics can be provided. The present embodiment is characterized by that the frame 250 and the interposer 220 are separated, and each of them have the optimum specification for mechanical and electrical properties.

Since the ultrasonic transducer unit 110 is provided necessary intensity by the frame 250, the interposer 220 can obtain the electrically optimum thickness. Since the ultrasonic transducer unit 110 is constituted by two components, i.e., the frame 250 and the interposer 220, the CMUT 107 with small parasitic capacitance of wires and excellent receiving characteristics while keeping machinery intensity necessary for the ultrasonic transducer unit 110 can be provided.

In the present embodiment, since the CMUT formed on the plane of the chip 190 is used, the planar ultrasonic transducer unit 110 can be implemented with an easy configuration only by combining the interposer 220 and the frame 250.

In the present embodiment, a photoacoustic probe with excellent receiving characteristics in a wideband and with a simple configuration of the wiring and the photoacoustic probe can be provided. Another form of the present embodiment is described with reference to FIGS. 7A and 7B.

The frame 250 holding the interposer 220 is fixed to the frame 120 in FIG. 7A, whereas the interposer 220 is fixed directly to the frame 120 without using the frame 250 in another form of FIG. 7B. In this form, the interposer 220 is desirably thicker than in a configuration with the frame 250 so that warpage or the like of the interposer 220 does not become a problem. In this another form, since no frame 250 is used, the number of components can be reduced, whereby the photoacoustic probe can be reduced in size and weight.

Here, a circuit of the receiving circuit 402 of the present embodiment is described with reference to FIG. 6C. In the present embodiment, a transimpedance circuit configuration using the operational amplifier 411 is employed as the receiving circuit 402.

The feedback resistance 412 and the feedback capacitance 413 are disposed parallel in a negative feedback portion of the operational amplifier 411, and a current input in the feedback portion is converted into a voltage. With the feedback characteristics of the operational amplifier 411, an influence of the parasitic capacitance on the input wiring can be reduced by using the broadband operational amplifier. Therefore, excellent receiving characteristics of the ultrasonic wave with reduced deterioration in current-voltage conversion can be obtained compared with a case where the receiving circuit 402 is disposed immediately close to the cell 200 (i.e., a case where the parasitic capacitance of the wiring is very small).

According to the present embodiment, since the transimpedance circuit configuration in which the operational amplifier 411 is used in the receiving circuit 402 is used, an influence of the capacitance parasitic in the input terminal of the receiving circuit 402 is less easily exerted. Therefore, a photoacoustic probe that is hardly affected by an influence of the parasitic capacitance of the group selection unit, and is reduced in deterioration in receiving characteristics can be provided.

Fourth Embodiment

In a fourth embodiment, a group selection unit is described. Other configurations are the same as those of the third and other embodiments. FIG. 8A schematically illustrates a group selection unit 130 of a photoacoustic probe according to the present embodiment. The present embodiment is characterized by that the group selection unit 130 is a switch 131, which is disposed between second electrodes 203 of CMUTs 107 and a receiving circuit 402.

Each CMUT 107 belonging to first to fourth groups is connected to one receiving circuit 402 via the group selection unit 130. Four CMUTs 107 connected to the same receiving circuit is referred to as a single element group. The group selection unit 130 specifically is a switch for turning on and off the connection between two terminals, and has a function to select one CMUT 107 to be connected to the receiving circuit 402 from the CMUTs 107 of the four groups.

In the group selection unit 130, the element selection signal 151 generated by the element selection signal generating unit 140 is input in accordance with the light-emitting timing of the light source 106. A first group G1, a second group G2, a third group G3, a fourth group G4, and the first group G1 are selected repeatedly in this order by the element selection signal 151.

A receiving circuit 402 of the present invention is a transimpedance circuit using an operational amplifier. A transimpedance circuit using an operational amplifier is characterized by that a decrease in current-voltage conversion efficiency is not easily caused due to parasitic capacitance at an input terminal. Therefore, the receiving characteristic of the photoacoustic wave does not deteriorate easily due to parasitic capacitance of the switch 131 disposed between the second electrode 203 of the CMUT 107 and the receiving circuit 402.

According to the present embodiment, since it is only necessary to provide the receiving circuit 402 for each element group, a photoacoustic probe capable of acquiring subject information, for reducing generation of artifacts with smaller number of receiving circuits 402 can be provided.

Fifth Embodiment

In a fifth embodiment, a group selection unit is described similarly. Other configurations are the same as those of the third and other embodiments. FIG. 8B schematically illustrates a describing group selection unit 130 of a photoacoustic probe according to the present embodiment. The present embodiment is characterized by that the group selection unit 130 is disposed between a first electrode 202 of a CMUT 107 and a DC voltage generating unit 401.

The group selection unit 130 of the present embodiment specifically is high breakdown voltage switches 132. By turning the high breakdown voltage switches 132 on and off, a DC high voltage applied to the first electrode 202 of the CMUTs 107 can be turned on and off.

The CMUT 107 receives the photoacoustic wave (i.e., the ultrasonic wave) when there is a potential difference between the first electrode 202 and the second electrode 203. If there is no potential difference between the first electrode 202 and the second electrode 203, no reception signal of the photoacoustic wave (i.e., the ultrasonic wave) is output.

In the present embodiment, the high breakdown voltage switch 132 connected to the CMUT 107 belonging to the selected group by the element selection signal 151 is ON. Therefore, a potential difference is produced between the electrodes of the CMUTs 107 belonging to the selected group, and the CMUTs 107 belonging to the selected group output detection signals in response to the photoacoustic wave the ultrasonic wave).

The high breakdown voltage switch 132 connected to the CMUT 107 belonging to a group that is not selected is OFF. Therefore, no potential difference is produced between the electrodes of the CMUTs 107 belonging to the groups that are not selected, and the CMUTs 107 belonging to the groups that are not selected are in the state of not outputting detection signals in response to the photoacoustic wave (i.e., the ultrasonic wave).

According to the present embodiment, since it is not necessary to dispose a switch between the second electrode and the receiving circuit. 402 like in the fourth embodiment, output noise of the receiving circuit 402 does not increase due to parasitic capacitance of the switch. A photoacoustic probe capable of acquiring subject information for reducing generation of artifacts without deterioration of the receiving characteristic of the photoacoustic wave can be provided.

Sixth Embodiment

In a sixth embodiment, a group selection unit is described similarly. Other configurations are the same as those of the third and other embodiments. FIGS. 9A and 9B schematically illustrate a group selection unit 130 of a photoacoustic probe according to the present embodiment.

As illustrated in FIG. 9A, the present embodiment is characterized by that the group selection unit 130 is disposed between a second electrode 203 of a CMUT 107 and a receiving circuit 402, and that a DC potential can be applied to the second electrode 203 by a second DC voltage generating unit 403.

FIG. 9B schematically illustrates a circuit of the group selection unit 130 of the present embodiment. In FIG. 9B, the reference numeral 133 denotes a high breakdown voltage switch, R denotes high breakdown voltage resistance, C denotes a high breakdown voltage capacitor, and D denotes a diode. The high breakdown voltage capacitor C is disposed between the second electrode 203 of the CMUT 107 and an input terminal of the receiving circuit 402. The high breakdown voltage resistance R and the high breakdown voltage switch 133 are disposed between the second electrode 203 and the DC voltage generating unit 401. The high breakdown voltage capacitor C is disposed between the second electrode 203 and the input terminal of receiving circuit 402. A capacitance value of the high breakdown voltage capacitor C is sufficiently greater than a capacitance value of the CMUT 107.

The high breakdown voltage switch 133 connected to the CMUT 107 belonging to the selected group by the element selection signal 151 is OFF. Therefore, a reference potential Vref that the receiving circuit 402 has is applied to the second electrode 203, and a potential difference is produced between the first electrode 202 and the second electrode 203.

In this configuration in which the vibration film 201 receives the photoacoustic wave (i.e., the ultrasonic wave), since the capacitance value of the high breakdown voltage capacitor C is sufficiently large, an AC microcurrent generated in the CMUT 107 is input in the input terminal of the receiving circuit 402. The current is converted into a voltage in the receiving circuit 402 and is then output.

The high breakdown voltage switch 133 connected to the CMUT 107 belonging to a group that is not selected is ON. Therefore, a potential generated in the DC voltage generating unit 401 is applied to the second electrode 203.

At this time, no potential difference exists between the first electrode 202 and the second electrode 203, and the CMUT 107 is not receiving.

Since the high breakdown voltage capacitor C is disposed between the second electrode 203 and the input terminal of the receiving circuit 402, no high voltage is applied to the input terminal of the receiving circuit 402.

Existence of the high breakdown voltage resistance R and the diode D avoids application of a surge voltage, upon switching OFF to ON of the high breakdown voltage switch 133 to the input terminal of the receiving circuit 402 and damage to the receiving circuit 402.

According to the present embodiment, since the element can be selected only by using the second electrodes 203 from the CMUTs 107, it is not necessary to increase the number of wires independently drawn out of the CMUTs 107.

Since parasitic capacitance applied to the input terminal of the receiving circuit 402 upon reception requires only one of the sides of the high breakdown voltage switch 133, an increase in output noise of the receiving circuit 402 due to the parasitic capacitance of the switch can be reduced to the minimum. Therefore, a photoacoustic probe for reducing generation of artifacts capable of acquiring subject information without increasing the number of wires from the transducer and with less deterioration in the receiving characteristics of the photoacoustic wave can be provided.

Seventh Embodiment

In a seventh embodiment, a group selection unit is described similarly. Other configurations are the same as those of the third and other embodiments. FIG. 10A schematically illustrates a group selection unit 130 of a photoacoustic probe according to the present embodiment. The present embodiment is characterized by including a receiving circuit 402 for each CMUT 107, and that the group selection unit 130 has a function to select output from the receiving circuit 402 connected to an external extraction wire.

Each CMUT 107 of a first group G1, a second group G2, a third group G3, and a fourth group G4 is equipped with a receiving circuit 402, respectively. The group selection unit 130 is disposed between the receiving circuit 402 and a cable 104. The group selection unit 130 of the present embodiment specifically is a switch 134 that connects the cable 104 and an output terminal of the receiving circuit 402 connected to each group.

According to the present embodiment, a photoacoustic probe for reducing generation of artifacts capable of acquiring subject information without the need of increasing the number of wires from the transducer, with no influence on the receiving characteristics of the photoacoustic wave since no configuration is added between the second electrode 203 and the input terminal of the receiving circuit 402.

Eighth Embodiment

In an eighth embodiment, a group selection unit is described similarly. Other configurations are the same as those of the seventh and other embodiments. FIGS. 10A and 10B schematically illustrate a group selection unit 130 of a photoacoustic probe according to the present embodiment. The present embodiment is characterized by that a receiving circuit 402 not connected to the CMUT 107 used for detection of signals of the photoacoustic wave is stopping the operation of an operational amplifier of a receiving circuit 402.

Therefore, as illustrated in FIG. 10B, the present embodiment is provided with a receiving circuit motion control unit 135. An element selection signal 151 generated by the element selection signal generating unit 140 is input in the receiving circuit motion control unit 135.

In the receiving circuit motion control unit 235, a receiving circuit 402 that is not used for generation of detection signals is determined in accordance with information on the selected groups included in the element selection signal 151, and the operation of the corresponding receiving circuit 402 is stopped.

Specifically, power supply to the receiving circuit 402 is stopped or generation of a bias current in the receiving circuit 402 is stopped.

In this manner, power consumption in the receiving circuit 402 that is not used for generation of detection signals can be reduced. Therefore, an increase in generated heat in the receiving circuit 402 can be reduced even if the number of CMUTs 107 increases.

In the period in which no photoacoustic wave (i.e., ultrasonic wave) is input from the subject in the CMUT 107, the operation of not only the receiving circuits 402 connected to the groups that are not selected, but all the receiving circuits 402 is desirably stopped.

Specifically, the operation of the receiving circuits 402 are desirably stopped except for the period after emission of light by the light source 106 until arrival, at the transducer, of the photoacoustic wave (ultrasonic wave) from the location furthest from the photoacoustic probe of the subject. In this manner, power consumption (i.e., heat generation) in the receiving circuit 402 can further be reduced.

According to the present embodiment, a photoacoustic probe for reducing generation of artifacts capable of acquiring subject information without the need of increasing the number of wires from the transducer, with no influence on the receiving characteristics of the photoacoustic wave, and with the smallest increase in power consumption can be provided.

Another form of the present embodiment is described with reference to FIG. 10C. The form of FIG. 10C is characterized by that an adder circuit (adder) 136 of AC signals is disposed between a receiving circuit 402 and a cable 104 connected to each group, and that a receiving circuit motion control unit 135 has a function of a group selection unit 130.

Since the receiving circuit 402 that has stopped operation detects no signal from the CMUT 107, the group is in a state equivalent to not being selected. AC components of the frequency of the photoacoustic wave of the detection signal from each group are added in the adder 136 and output to the cable 104 as output signals. With the existence of the adder 136, a function to select a group can be provided by selecting and stopping the operation of the receiving circuit 402. Since this another form does not need to include a switch 134, a simpler configuration is implemented with no need to increase the number of wires from the transducer.

Ninth Embodiment

In a ninth embodiment, a group to be selected is described. Other configurations are the same as those of the first to the eighth embodiments. FIGS. 11A to 11D schematically illustrate grouping of a photoacoustic probe according to the present embodiment. The present embodiment is characterized by having a function to select the element of the CMUT 107 not in the element unit but by shifting the element by half, and output detection signals.

In the present embodiment, when one group is selected, four element positions can be selected. Specifically, a first element position as illustrated in FIG. 11A, a second element position b illustrated in FIG. 11B, a third element position c illustrated in FIG. 11C, and a fourth element position d illustrated in FIG. 11D can be selected sequentially. Here, a region of a group to be selected by the group selection unit can be considered as overlapping with a region of another group.

According to the present embodiment, a photoacoustic probe capable of detecting a photoacoustic wave at an intermediate position of a plurality of elements without increasing the number of elements, and capable of acquiring information from a subject in more detail can be provided.

Tenth Embodiment

In a tenth embodiment, a group selection unit is described. Other configurations are the same as those of ninth and other embodiments. FIGS. 12A, 12B, 13A and 13B schematically illustrate grouping of a photoacoustic probe according to the present embodiment. The present embodiment is characterized by being constituted by subelements which are four divisions of an element, including a switch 235 for connecting adjoining subelements, and a receiving circuit 402 for each group, and including an adder circuit 137 for adding outputs from four receiving circuits 402. Here, it is also possible to constitute a group to be selected by the group selection unit by a collection of subelements equally divided in the group.

Further, it is also possible to constitute the CMUT using a rectangular first subelement region, a second subelement region which adjoins to the upper and lower sides of the first subelement, a third subelement region which adjoins to the left and right sides of the first subelement, and a fourth subelement region which adjoins to a corner of the first subelement.

FIG. 12A illustrates a state where the first element position a of the first group G1 is selected in FIG. 11A. In the present embodiment, an element is divided into four subelements, and the switch 235 for connecting adjacent subelements is provided. Therefore, subelements in the region to be selected are connectable.

The receiving circuit 402 is connected to one of the four subelements which are four divisions of an element.

FIG. 12A illustrates a configuration in which the receiving circuit 402 is connected to the upper left subelement among the four subelements which are four divisions of an element. The present embodiment is characterized by that a distance between the subelements to which the receiving circuit 402 is connected is substantially the same. Signals from the receiving circuits 402 of the four groups are added in an adder circuit 137 and output to the cable 104.

Similarly, it can be selected sequentially as illustrated in FIG. 12B when the second element position b in FIG. 11B is selected, as illustrated in FIG. 13A when the third element position c in FIG. 11C is selected, and as illustrated in FIG. 13B when the fourth element position d in FIG. 11D is selected.

The element positions can also be selected not only for the first group G1 but for the second group G2, the third group G3, and the fourth group G4.

According to the present embodiment, a photoacoustic probe capable of providing a function to detect a photoacoustic wave at an intermediate position of a plurality of elements by a simple circuit configuration without increasing the number of elements.

Eleventh Embodiment

In an eleventh embodiment, a group selection unit is described similarly. Other configurations are the same as those of the third to the ninth embodiments. FIGS. 14A to 14D, 15A, 15B, 16A and 16B schematically illustrate grouping of the photoacoustic probe according to the present embodiment.

The present embodiment is characterized by being divided into a first subelement region R1, a second subelement region R2, a third subelement region R3, and a fourth subelement region R4 each constituted by a plurality of subelements. The present embodiment is characterized also by having adder circuits 137 and 139 that select and add a detection signal from each region adjoining the first subelement region to a detection signal from the first subelement region, and having a wire selection unit 138.

The first region R1 is constituted by 3×3 subelements, and it is possible to select from which subelement a detection signal is output. The selection can be suitably performed using the group selection unit 130 described in the fourth to the eighth embodiments. The first regions R1 are arranged two-dimensionally and periodically at intervals, and regions where no first subelement region R1 is disposed form a grid pattern.

The region at which grids of the grid pattern cross each other is referred to as the fourth subelement region R4, the horizontally elongated region located between a plurality of fourth regions R4 is referred to as the second region R2, and the vertically elongated region located between a plurality of fourth regions R4 is referred to as the third region R3. Specifically, the fourth region R4 is constituted by one subelement, the second region R2 is constituted by 3×1 subelements, and the third region R3 is constituted by 1×3 subelements. Regarding the second region R2 and the third region R3, from which subelement the detection signal is output can be selected.

With the adder circuit 137, an output signal from two second subelement regions R2 adjoining to the first subelement region R1 and an output signal from two third subelement regions R3 adjoining to the first subelement region R1 can be selected and added. With the wire selection unit 138, an output signal from four fourth subelement regions R4 adjoining to the first subelement region R1 can be selected and output. With an adder circuit (adder) 139, these two added signals are added to the detection signal of the first subelement region R1, and are output to the cable 104 (113) as an output signal.

FIG. 14A illustrates a state where the upper left 2×2 region of the first subelement region R1 is selected.

At this time, as schematically illustrated in FIG. 15A, no signal to be added is input and no addition is performed in the adder circuit 137. In the wire selection unit 138, no signal is selected and no signal is output to the adder 139. Therefore, signals passed through the adder 139 are only those detected in the upper left 2×2 region selected in the first subelement region R1, and are output via the wire 104 (113) as they are.

FIG. 14B illustrates a state where the lower left 1×2 region of the first subelement region R1 and the 1×2 region of the third subelement region adjoining to the first subelement region R1 on the left are selected. At this time, as schematically illustrated in FIG. 15B, in the adder circuit 137, signals from the third subelement region on the left of the first subelement region R1 are selected and output as they are.

In the wire selection unit 138, no signal is selected, and no signal is output to the adder 139. Therefore, in the adder 139, a signal detected in the lower 1×2 region of the third subelement region adjoining to the first subelement region R1 on the left is added to a signal detected in the selected lower left 1×2 region of the first subelement region R1, and is output via the wire 104 (113).

FIG. 14C illustrates a state where the upper left 1×1 region of the first subelement region R1, one leftmost region of the second subelement region adjoining to the first subelement region R1 on the upper side, one uppermost region of the third subelement region adjoining to the first subelement region R1 on the left, and the upper left fourth subelement region adjoining to the first subelement region R1 are selected.

At this time, as schematically illustrated in FIG. 14C, in the adder circuit 137, a signal from the second subelement region adjoining to the first subelement region R1 on the upper side and a signal from the third subelement region adjoining to the first subelement region R1 on the left are added and output.

In the wire selection unit 138, an output signal from the fourth subelement region R4 on the upper left of the first subelement region R1 is selected.

Therefore, in the adder 139, to the signal detected in the selected upper left 1×1 region of the first subelement region R1, a signal detected at the leftmost region of the second subelement region adjoining to the first subelement region R1 on the upper side, a signal detected at the uppermost region of the third subelement region adjoining to the first subelement region R1 on the left, and an output signal from the upper left fourth subelement region R4 are added and output via the wire 104 (113).

FIG. 14D illustrates a state where the lower right 1×1 region of the first subelement region R1, one rightmost region of the second subelement region adjoining to the first subelement region R1 on the lower side, one lowermost region of the third subelement region adjoining to the first subelement region R1 on the right, and the lower right fourth subelement region adjoining to the first subelement region R1 are selected.

At this time, as schematically illustrated in FIG. 15D, in the adder circuit 137, a signal from the second subelement region adjoining to the first subelement region R1 on the lower side, and a signal from the third subelement region adjoining to the first subelement region R1 on the right are selected, added and output. In the wire selection unit 138, an output signal from the fourth subelement region R4 on the lower right of the first subelement region R1 is selected.

Therefore, in the adder 139, to the signal detected in the selected lower right 1×1 region of the first subelement region R1, a signal detected at the rightmost region of the second subelement region adjoining to the first subelement region R1 on the lower side, a signal detected at the lowermost region of the third subelement region adjoining to the first subelement region R1 on the right, and an output signal from the lower right fourth subelement region R4 are added and output via the wire 104 (113).

As described above, in the present embodiment, a photoacoustic wave can be detected by selecting an arbitrary region with a simple configuration in which signals of the peripheral second to the fourth subelements are selected and added about the first subelement region R1.

Twelfth Embodiment

In a twelfth embodiment, a group selection unit is described similarly. Other configurations are the same as those of the first to the eleventh embodiments. FIGS. 17, 18A and 18B schematically illustrate grouping of a photoacoustic probe according to the present embodiment. The present embodiment is characterized in that, as illustrated in FIG. 17, a group selection unit 130 is disposed between a photoacoustic wave receiving surface of an ultrasonic transducer 103 (107) and a subject.

In the group selection unit 130 of the present embodiment, an acoustic wave transmission selection unit 160 capable of selecting whether an acoustic wave is to be transmitted is disposed in each photoacoustic wave receiving element of the ultrasonic transducer (i.e., element). The output of the ultrasonic transducer 103 (107) is added to the detection signal and is output to the cable 104 (113).

As schematically illustrated in FIGS. 18a and 18b, the acoustic wave transmission selection unit 160 selects whether the acoustic wave 153 is to be transmitted in accordance with the element selection signal 151. The acoustic wave (i.e., the ultrasonic wave) penetrates (155) the acoustic wave transmission selection unit 160 and arrives at a surface of the element of the selected group. In an element which is not selected, the acoustic wave (i.e., the ultrasonic wave) is reflected (154) on the acoustic wave transmission selection unit 160 and does not arrive at an element surface. Therefore, only the acoustic wave (i.e., the ultrasonic wave) arrived at the element position of the selected group can be detected and output.

A specific configuration of the acoustic wave transmission selection unit 160 is described with reference to FIGS. 18A and 18B. In the acoustic wave transmission selection unit 160, a movable film 161 is disposed above a support member 163 that transmits an ultrasonic wave by pillars 162, and a cavity 164 exists between the support member 163 and the movable film 161. The movable film 161 is excellent in transmission characteristics of the ultrasonic wave, and is not vibrated by the ultrasonic wave.

When the element selection signal 151 is input, fore to cause the support member 163 and the movable film 161 to adhere to each other occurs, leaving substantially no region for the cavity 164. The means for adhering the support member 163 and the movable film 161 to each other may be electrostatic force, electromagnetic force, a piezoelectric element, and so on.

When no element is selected, as illustrated in FIG. 18A, a cavity 164 exists in the support member 163 and the movable film 161.

The ultrasonic wave is reflected due to a difference of an acoustic impedance on an interface with the cavity 164, and does not penetrate to the transducer side. When the element is selected, as illustrated in FIG. 18B, the support member 163 and the movable film 161 adhere to each other in the most area thereof with no cavity 164 left. Therefore, the ultrasonic wave 153 proceeds inside the movable film 161 and the support member 163, and penetrates to the transducer side.

According to the present embodiment, a photoacoustic wave (i.e., an ultrasonic wave) that arrives at an element can be selected with a simple configuration. Therefore, a photoacoustic probe capable of acquiring subject information for reducing generation of artifacts without complication of the configuration of the electric circuit and without increasing the number of wires connected to output signals outside can be provided.

Thirteenth Embodiment

In a thirteenth embodiment, a receiving circuit is described. Other configurations are the same as those of any of the third to the twelfth embodiments. FIGS. 19A and 19B schematically illustrate a receiving circuit of a photoacoustic probe according to the present embodiment.

The present embodiment is characterized by including, instead of the receiving circuit 402, a drive receiving circuit 421 having a function not only to detect a photoacoustic wave (i.e., an ultrasonic wave) received by the CMUT 107 as a signal, but apply (i.e., transmit) the ultrasonic wave to a subject from the CMUT 107.

In FIGS. 19A and 19B, the reference numeral 421 denotes a drive receiving circuit, 431 denotes an operational amplifier, 432 denotes a feedback resister, 433 denotes feedback capacitance, 434 and 435 denote high breakdown voltage, switches, 436 and 437 denote diodes, and 438 denotes a high breakdown voltage diode.

FIG. 19A schematically illustrates a state where an electrostatic transducer 107 is disposed on a chip 190. A single element of the CMUT 107 is disposed on each chip, and a second, electrode 203 of the transducer 107 is connected to the drive receiving circuit 421.

The drive receiving circuit 421 has a function to apply, to the CMUT 107, high voltage pulses used for transmission of the ultrasonic wave from the apparatus, and output a micro-current from the CMUT 107 as detection signals to the apparatus.

FIG. 19B is a circuit diagram illustrating the drive receiving circuit 421. A feedback resister 432 and a feedback capacitance 433 are disposed in parallel at a negative feedback portion of an operational amplifier 431, and have a function to perform current-voltage conversion. A high breakdown voltage switch 434, the diode 436 are connected to an input terminal of the operational amplifier 431 and the high breakdown voltage switch 435 and the diode 437 are connected to an output terminal of the operational amplifier 431.

In the high breakdown voltage diode 438, wire connection between terminals is disconnected when the voltage between terminals becomes a predetermined value or smaller (i.e., 1 v or smaller). When a voltage higher than a predetermined voltage (i.e., about several volts) is applied to the high breakdown voltage switches 434 and 435, wires between I/O terminals of the switches are disconnected.

When no high voltage pulse for transmission is applied, there is substantially no potential difference between the terminals in the high breakdown voltage diode 439, and therefore the wires in the I/O terminal in the high breakdown voltage diode 439 are disconnected.

Wires between the switches in the high breakdown voltage switches 434 and 435 are connected since no high voltage is applied from the outside. Therefore, the micro-current from the transducer can be converted into a voltage in the operational amplifier, and detection signals can be output to an apparatus connected to the outside (not illustrated).

When high voltage pulses for transmission are applied from the apparatus (not illustrated), the wires inside the high breakdown voltage diode 439 are connected, and a voltage higher than a predetermined voltage (i.e., about several volts) is applied to the high breakdown voltage switches 434 and 435. Therefore, the high breakdown voltage switches 434 and 435 disconnect the wires inside thereof. In this manner, damage to the operational amplifier due to application of a high voltage thereto can be avoided.

Since a signal output from the operational amplifier is cut by the high breakdown voltage switch 435, no influence is exerted on the high voltage pulses applied for the transmission. Therefore, the high voltage pulses for transmitting the ultrasonic wave to the first electrode of the transducer can be applied.

According to the present embodiment, a single photoacoustic probe is capable of receiving the photoacoustic wave, and is capable of transmitting and receiving the ultrasonic wave. Therefore, a photoacoustic image and an ultrasonic image can be formed in accordance with the detected data.

Since the CMUT 107 is used for receiving the photoacoustic wave and for transmitting and receiving the ultrasonic wave, a photoacoustic image and an ultrasonic image with reduced misalignment can be obtained.

Fourteenth Embodiment

The photoacoustic probe described in the first to the thirteenth embodiments can be used for the reception of the photoacoustic wave (i.e., the ultrasonic wave) using the photoacoustic effect, and can be applied to a subject information acquisition apparatus provided with the same. An operation of the subject information acquisition apparatus of the present embodiment is described with reference to FIG. 20A.

First, in accordance with a light emission instruction signal 701, a light source 805 generates light 702. (i.e., pulsed light) with which a measurement target 800 is irradiated. In the measurement target 800, a photoacoustic wave (i.e., an ultrasonic wave) 703 is generated upon irradiation of the light 702. The ultrasonic wave 703 is received by a plurality of CMUTs 802 of the photoacoustic probe. Information on the magnitude, shape, and time of the reception signal is transmitted to an image information generating apparatus 803 as photoacoustic wave reception signals 704.

The information on the magnitude, shape, and time of the light 702 generated by the light source 805 (light emission information) is stored in the image information generating apparatus 803 of the photoacoustic signal. In the image information generating apparatus 803 of the photoacoustic signal, image signals of the measurement target 800 is generated in accordance with the photoacoustic wave reception signals 704 and the light emission information, and output as reproduction image information 705 by the photoacoustic signal. An image display unit 804 displays the measurement target 800 as an image in accordance with the reproduction image information 705 by the photoacoustic signal.

The photoacoustic probe according to the present embodiment has high operability, and is capable of generating a high quality photoacoustic wave image with less artifacts because it does not need to increase the number of wires even if the ultrasonic transducers are arranged with high density.

Fifteenth Embodiment

The present embodiment is a form in the thirteenth photoacoustic probe is used for the subject information acquisition apparatus of the fourteenth embodiment. FIG. 20B schematically illustrates a subject information acquisition apparatus according to the present embodiment. In FIG. 20B, the reference numeral 706 denotes a transmission and reception signal of an ultrasonic wave, 707 denotes a transmitted ultrasonic wave, 708 denotes a reflected ultrasonic wave, and 709 denotes reproduction image information by transmission and reception of an ultrasonic wave.

In addition to the reception of the photoacoustic wave, the subject information acquisition apparatus of the present embodiment performs pulse echo (i.e., transmission and reception of the ultrasonic wave) and forms an image. Since reception of the photoacoustic wave is the same as that of the twelfth embodiment, the pulse echo (i.e., transmission and reception of the ultrasonic wave) is described here.

In accordance with the transmission signal of the transmission and reception signal 706 of the ultrasonic wave, an ultrasonic wave 706 is output (i.e., transmitted) to the measurement target 800 from a plurality of CMUTs 802. The ultrasonic wave is reflected inside the measurement target 800 due to a difference of a specific acoustic impedance of objects exist therein. Reflected ultrasonic wave 708 is received by a plurality of CMUTs 802, and information on magnitude of reception signal, shape, and time is sent to image information generating apparatus 803 as reception signal of the transmission and reception signal 706.

The information on the magnitude, shape, and time of the transmitted ultrasonic wave is stored in the image information generating apparatus 803 as ultrasonic wave transmission information. The image information generating apparatus 803 generates image signals of the measurement target 800 in accordance with the reception signal of the transmission and reception signal 706 and ultrasonic wave transmission information, and outputs the image signals as reproduction image information 709 of ultrasonic wave transmission and reception. The image display unit 804 displays the measurement target 800 as an image in accordance with two pieces of information, i.e., the reproduction image information 705 by the photoacoustic signal, and the reproduction image information 709 by the ultrasonic wave transmission and reception.

The photoacoustic probe according to the present embodiment has high operability, and is capable of generating a high quality photoacoustic wave image with less artifacts, and acquiring a high quality ultrasonic image with less artifacts.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-242445, filed Nov. 28, 2014 and No. 2015-218781, filed Nov. 6, 2015, which are hereby incorporated by reference herein in their entirety.

REFERENCE SIGNS LIST 100 photoacoustic probe
103 Ultrasonic transducer
130 Group selection unit

The invention claimed is:

1. A probe, comprising:
a plurality of ultrasonic transducers divided into a plurality of groups and configured to receive photoacoustic waves from a subject irradiated by a light source;
a plurality of receiving circuits connected to the plurality of ultrasonic transducers and configured to generate detection signals based on the received photoacoustic waves; and
a group selection unit configured to switch signals corresponding to the received photoacoustic waves to be output for each of the groups based on a selection signal,
wherein the receiving circuits are provided respectively for the groups,
wherein a first ultrasonic transducer belonging to a first group of the plurality of groups is surrounded by other ultrasonic transducers belonging to different groups of the plurality of groups that are different from the first group, and
wherein the group selection unit outputs a signal for stopping operation of the receiving circuit that corresponds to the group that does not output the signals.

2. The probe according to claim 1, wherein the signals of the ultrasonic transducers are output via wires.

3. The probe according to claim 1, wherein distances between the first ultrasonic transducer and closest ultrasonic transducers belonging to the different groups are substantially the same for each group.

4. The probe according to claim 1, wherein two ultrasonic transducers belonging to the same group are separated from each other, and an ultrasonic transducer belonging to another group is disposed between the two ultrasonic transducers belonging to the same group.

5. The probe according to claim 1, wherein the plurality of ultrasonic transducers are disposed on a curved surface.

6. The probe according to claim 1, wherein the ultrasonic transducer is provided with a plurality of cells each having a pair of electrodes formed with a space therebetween.

7. The probe according to claim 6, further comprising a voltage generating unit configured to apply a voltage between the pair of electrodes of the cell,
wherein the group selection unit is disposed between the ultrasonic transducer and the voltage generating unit, and
wherein the group selection unit operates such that there is no potential difference between the electrodes of the cell of the ultrasonic transducer belonging to the group that does not output the signals.

8. The probe according to claim 1, wherein a region of a group selected by the group selection unit overlaps with a region of another group.

9. The probe according to claim 1, wherein:
the plurality of ultrasonic transducers is constituted by a first subelement region, a second subelement region which adjoins to the upper and lower sides of the first subelement region, a third subelement region which adjoins to the left and right sides of the first subelement region, and a fourth subelement region which adjoins to a corner of the first subelement region;
the group selection unit is capable of selecting an arbitrary element for each of the first subelement region, the second subelement region, and the third subelement region; and
the probe is capable of selecting signals from the second subelement region, the third subelement region and the fourth subelement region, adding the signals to a signal from the first subelement region, and outputting to a wire,
wherein an adder circuit sums the detection signals outputted from the receiving circuits connected respectively to the first subelement region, the second subelement region, the third subelement region and the fourth subelement region.

10. The probe according to claim 1, wherein the group selection unit includes a transmission selection unit that has a movable film and a support member and causes one of the received photoacoustic waves to reflect on the movable film or to penetrate through the support member according to the selection signal.

11. A subject information acquisition apparatus comprising:
the probe according to claim 1;
an image information generating apparatus to generate reproduction image information from signals received from the probe; and
a display to display an image in accordance with the reproduction image information.

12. The subject information acquisition apparatus according to claim 11, wherein the probe is capable of transmitting an ultrasonic wave.

13. The probe according to claim 1, wherein the plurality of transducers are disposed on a hemispherical housing.

14. The probe according to claim 1 wherein the group selection unit switches the signals in synchronization with a light-emitting timing of the light source.

* * * * *